US008939988B2

United States Patent
Auerbach et al.

(10) Patent No.: US 8,939,988 B2
(45) Date of Patent: Jan. 27, 2015

(54) UTERINE MANIPULATORS AND RELATED COMPONENTS AND METHODS

(75) Inventors: Robert D. Auerbach, Madison, CT (US); Charles Sherts, Westport, CT (US); Peter K. Arneson, Cheshire, CT (US); Kerry Blair, Overland Park, KS (US)

(73) Assignee: CooperSurgical, Inc., Trumbull, CT (US)

( * ) Notice: Subject to any disclaimer, the term of this patent is extended or adjusted under 35 U.S.C. 154(b) by 595 days.

(21) Appl. No.: 12/916,986

(22) Filed: Nov. 1, 2010

(65) Prior Publication Data

US 2012/0109146 A1    May 3, 2012

(51) Int. Cl.
| | |
|---|---|
| A61B 17/42 | (2006.01) |
| A61B 17/00 | (2006.01) |
| A61B 17/29 | (2006.01) |
| A61B 17/32 | (2006.01) |
| A61B 19/00 | (2006.01) |

(52) U.S. Cl.
CPC ..... *A61B 17/4241* (2013.01); *A61B 2017/0046* (2013.01); *A61B 2017/00477* (2013.01); *A61B 2017/00557* (2013.01); *A61B 2017/2927* (2013.01); *A61B 2017/320052* (2013.01); *A61B 2019/4842* (2013.01)
USPC ......................................... 606/119

(58) Field of Classification Search
USPC ........................... 606/119, 135, 193; 604/271
See application file for complete search history.

(56) References Cited

U.S. PATENT DOCUMENTS

| | | | |
|---|---|---|---|
| 1,856,295 | A | 5/1932 | Sovatkin |
| 2,186,143 | A | 1/1940 | Neugass |
| 2,456,806 | A | 12/1948 | Wolffe |
| 2,744,708 | A | 5/1956 | Bedford, Jr. |
| 3,096,764 | A | 7/1963 | Hiebert |
| 3,131,690 | A | 5/1964 | Innis et al. |
| 3,153,267 | A | 10/1964 | Rowland, Jr. |
| 3,196,865 | A | 7/1965 | Rose |
| 3,749,088 | A | 7/1973 | Kohlmann |
| 3,766,909 | A | 10/1973 | Ozbey |
| 3,769,983 | A | 11/1973 | Merav |
| 3,877,433 | A | 4/1975 | Librach |
| 3,878,848 | A | 4/1975 | Hiebert |
| 3,948,270 | A | 4/1976 | Hasson |
| 4,022,208 | A | 5/1977 | Valtchev |

(Continued)

FOREIGN PATENT DOCUMENTS

| | | |
|---|---|---|
| DE | 20110921 | 12/2001 |
| DE | 69532474 | 11/2004 |

(Continued)

OTHER PUBLICATIONS

Culligan et al., "Long-Term Success of Abdominal Sacral Colpopexy Using Synthetic Mesh," Am. J. Obstet. Gynecol., Dec. 2002.

(Continued)

*Primary Examiner* — Thomas McEvoy
*Assistant Examiner* — Julie A Szpira
(74) *Attorney, Agent, or Firm* — Fish & Richardson P.C.

(57) ABSTRACT

A colpotomizer cup includes a cup body and a sleeve. The cup body is configured to receive a cervix. The sleeve is connected to the cup body and includes a locking member for locking the colpotomizer cup in a predetermined position along a length of the uterine manipulator handle.

27 Claims, 36 Drawing Sheets

(56) References Cited

U.S. PATENT DOCUMENTS

| | | |
|---|---|---|
| 4,066,071 A | 1/1978 | Nagel |
| 4,323,057 A | 4/1982 | Jamieson |
| 4,430,076 A | 2/1984 | Harris |
| 4,533,349 A | 8/1985 | Bark |
| 4,562,832 A | 1/1986 | Wilder et al. |
| 4,597,030 A | 6/1986 | Brody et al. |
| 4,627,421 A | 12/1986 | Symbas et al. |
| 4,775,362 A | 10/1988 | Kronner |
| 4,807,625 A | 2/1989 | Singleton |
| 4,823,167 A | 4/1989 | Manska et al. |
| 4,981,355 A | 1/1991 | Higgins |
| 4,996,974 A | 3/1991 | Ciarlei |
| 4,997,419 A | 3/1991 | Lakatos et al. |
| 5,059,198 A | 10/1991 | Gimpelson |
| 5,104,377 A | 4/1992 | Levine |
| 5,174,276 A | 12/1992 | Crockard |
| 5,181,842 A | 1/1993 | Sunderland et al. |
| 5,209,754 A * | 5/1993 | Ahluwalia ............ 600/207 |
| 5,232,443 A | 8/1993 | Leach |
| 5,237,985 A | 8/1993 | Hodgson et al. |
| 5,242,240 A | 9/1993 | Gorham |
| 5,259,836 A | 11/1993 | Thurmond et al. |
| 5,273,026 A | 12/1993 | Wilk |
| 5,338,297 A | 8/1994 | Kocur et al. |
| 5,353,784 A * | 10/1994 | Nady-Mohamed ........... 600/205 |
| 5,409,496 A | 4/1995 | Rowden et al. |
| 5,431,662 A | 7/1995 | Nicholas |
| 5,520,698 A * | 5/1996 | Koh ........................ 606/119 |
| 5,540,700 A * | 7/1996 | Rowden et al. ............ 606/119 |
| 5,549,563 A * | 8/1996 | Kronner ................ 604/170.03 |
| 5,571,115 A * | 11/1996 | Nicholas ................... 606/119 |
| 5,624,399 A | 4/1997 | Ackerman |
| 5,643,285 A * | 7/1997 | Rowden et al. ............ 606/119 |
| 5,690,617 A | 11/1997 | Wright |
| 5,810,806 A | 9/1998 | Ritchart et al. |
| 5,835,657 A | 11/1998 | Suarez et al. |
| 5,840,077 A * | 11/1998 | Rowden et al. ............ 606/119 |
| 6,068,121 A | 5/2000 | McGlinch |
| 6,080,118 A | 6/2000 | Blythe |
| 6,159,170 A | 12/2000 | Borodulin et al. |
| 6,328,729 B1 | 12/2001 | Jervis |
| 6,348,036 B1 | 2/2002 | Looney et al. |
| 6,423,075 B1 * | 7/2002 | Singh et al. ................... 606/119 |
| 6,651,992 B1 | 11/2003 | Smith |
| 6,682,100 B2 | 1/2004 | Wood et al. |
| 6,741,895 B1 | 5/2004 | Gafni et al. |
| 6,752,819 B1 | 6/2004 | Brady et al. |
| 6,932,759 B2 | 8/2005 | Kammerer et al. |
| 7,052,453 B2 | 5/2006 | Presthus et al. |
| 7,334,503 B1 | 2/2008 | Newman |
| 2001/0021854 A1 * | 9/2001 | Donnez et al. ................. 606/119 |
| 2003/0187334 A1 | 10/2003 | Biswas |
| 2003/0195386 A1 | 10/2003 | Thierfeld et al. |
| 2003/0220538 A1 | 11/2003 | Jacquetin |
| 2004/0138528 A1 | 7/2004 | Richter et al. |
| 2004/0193043 A1 | 9/2004 | Duchon et al. |
| 2004/0230092 A1 | 11/2004 | Thierfeld et al. |
| 2005/0065395 A1 | 3/2005 | Mellier |
| 2005/0085827 A1 * | 4/2005 | G. et al. ......................... 606/119 |
| 2005/0107818 A1 | 5/2005 | Valtchev |
| 2005/0277948 A1 | 12/2005 | Cedars |
| 2006/0015001 A1 | 1/2006 | Staskin et al. |
| 2006/0199994 A1 | 9/2006 | Inman et al. |
| 2006/0241652 A1 * | 10/2006 | Doll et al. ..................... 606/119 |
| 2007/0088351 A1 | 4/2007 | Ewaschuk et al. |
| 2007/0129615 A1 | 6/2007 | Backman et al. |
| 2008/0221590 A1 | 9/2008 | Ikeda et al. |
| 2008/0243176 A1 | 10/2008 | Weitzner et al. |
| 2008/0249535 A1 | 10/2008 | Valtchev |
| 2009/0131954 A1 * | 5/2009 | Christian et al. ............. 606/119 |
| 2010/0106163 A1 * | 4/2010 | Blair et al. .................... 606/119 |
| 2010/0152749 A1 | 6/2010 | Von Pechmann et al. |
| 2010/0168784 A1 | 7/2010 | Pustilnik |
| 2010/0179575 A1 | 7/2010 | Von Pechmann et al. |
| 2010/0280309 A1 | 11/2010 | Von Pechmann |
| 2011/0130769 A1 | 6/2011 | Boebel et al. |

FOREIGN PATENT DOCUMENTS

| | | |
|---|---|---|
| DE | 10341561 | 4/2005 |
| EP | 0400458 | 12/1990 |
| EP | 0890342 | 1/1999 |
| WO | WO 2008/074054 | 6/2008 |
| WO | WO 2009/078953 | 6/2009 |

OTHER PUBLICATIONS

"KOH Cup Vaginal Fornices Delineator & Colpo-Pneumo Occluder," *The Koh Colpotomizer™ System*, Directions for Use; 6 pages; Sep. 2008.

"Laparoscopic Hysterectomy and Colpotomy Accessories for Use Exclusively with the RUMI System Uterine Manipulator," *CooperSurgical The KOH Colpotomizer System*; 2 pages; Oct. 2006.

* cited by examiner

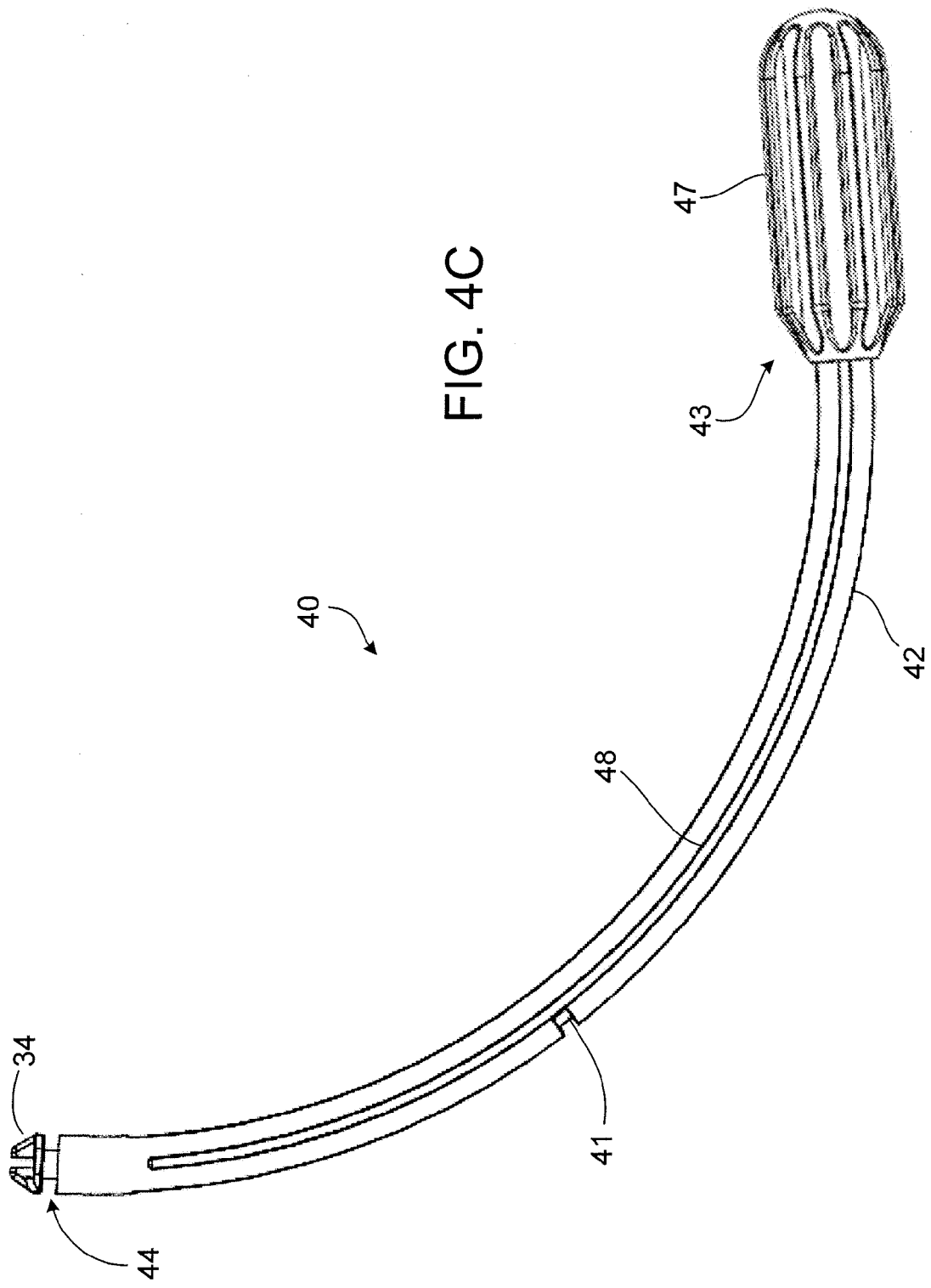

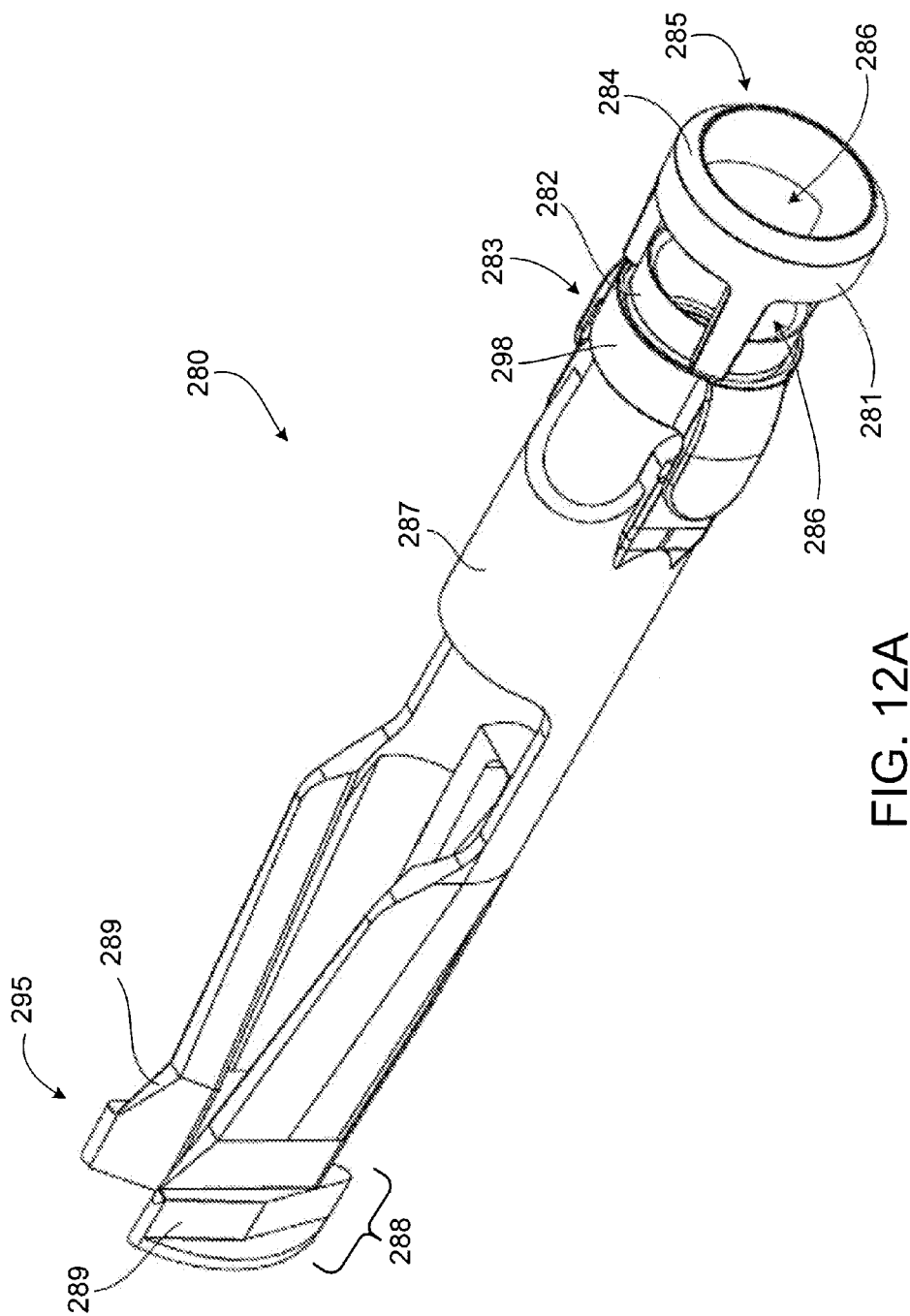

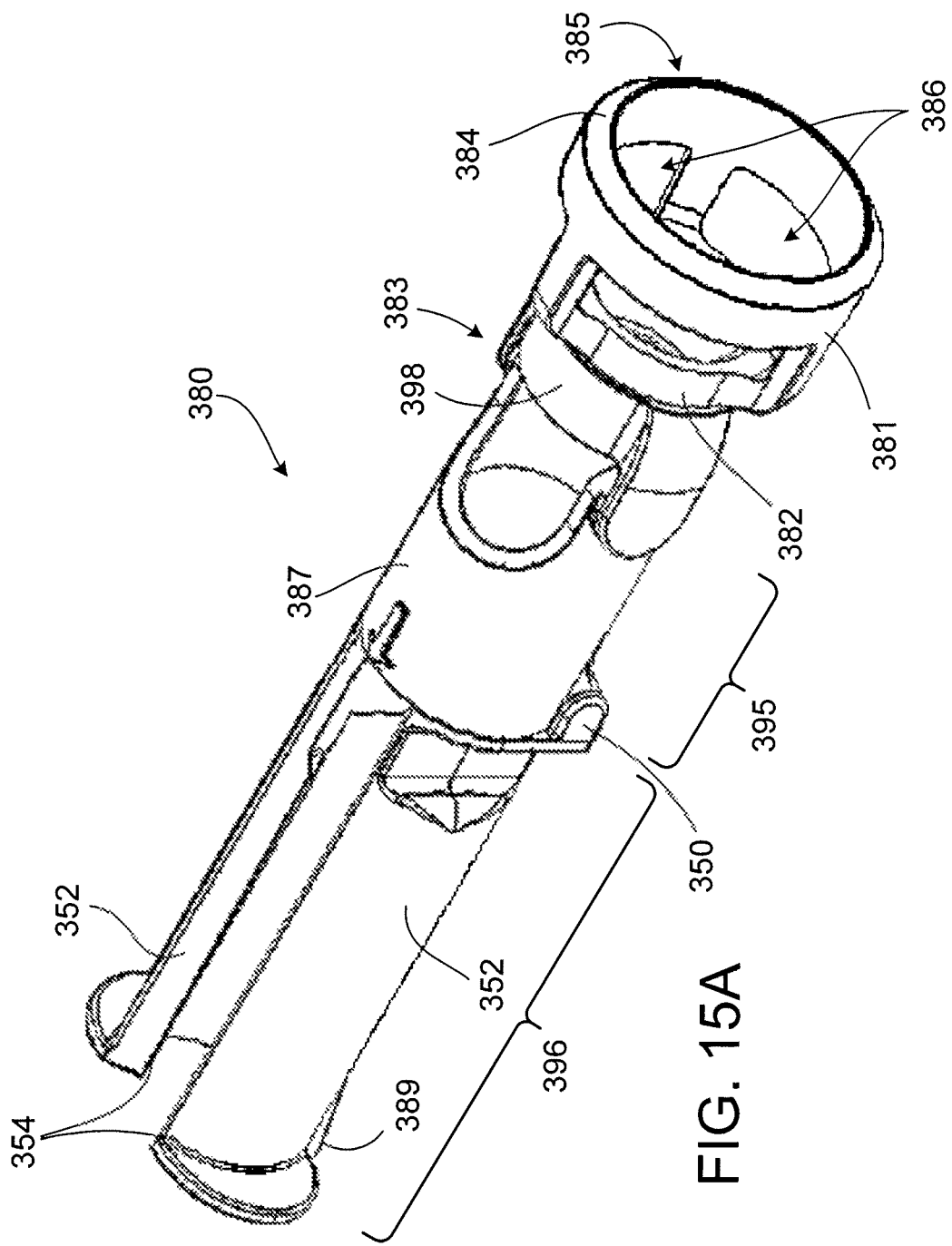

UTERINE MANIPULATORS AND RELATED COMPONENTS AND METHODS

TECHNICAL FIELD

This disclosure relates to uterine manipulators and related components and methods.

BACKGROUND

Uterine manipulators are medical instruments that are used for manipulating (e.g., moving or repositioning) a patient's uterus during medical procedures. Such procedures include surgical procedures such as laparoscopic gynecologic surgery, e.g., total laparoscopic hysterectomy (TLH) surgery.

Instruments of this kind often include a proximal portion that remains external to the patient's body during use and a distal portion that is inserted into the patient's body. The proximal portion typically provides for manipulation of the instrument during use. The distal portion often includes a tip that is sized to be inserted into and/or engage a uterus. Generally, the distal portion of the instrument is advanced through the vaginal cavity and into the uterus. With the distal portion inserted within a uterus, the uterus can be manipulated through surgeon or physician controlled movements of the proximal portion. Following completion of a procedure, the instrument is removed from the patient's body via the vaginal cavity.

SUMMARY

In general, this disclosure relates to uterine manipulators and related components (e.g., colpotomizer cups) and methods. The uterine manipulators can be used, for example, for manipulating a patient's uterus during gynecological surgery and/or gynecological diagnostic procedures.

In one aspect, a colpotomizer cup includes a cup body configured to receive a cervix, and a sleeve connected to the cup body. The sleeve includes a locking member for locking the colpotomizer cup in a predetermined position along a length of the uterine manipulator handle.

In another aspect, a uterine manipulator includes a uterine manipulator handle including a locking feature, and a colpotomizer cup. The colpotomizer cup includes a cup body configured to receive a cervix, and a sleeve connected to the cup body. The sleeve includes a locking member configured to engage the locking feature of the uterine manipulator handle for locking the colpotomizer cup in a predetermined, locked position along a length of the uterine manipulator handle.

In a further aspect, a method includes inserting a uterine manipulator comprising a manipulator handle and a manipulator tip into a vaginal cavity such that a finger of the manipulator tip extends into a cervix of a uterus; and then sliding a colpotomizer cup along the manipulator handle, towards the manipulator tip, until a locking member on a sleeve of the colpotomizer cup engages a locking feature of the manipulator handle.

Implementations may provide one or more of the following features.

In some implementations, the colpotomizer cup includes a vaginal occluder.

In certain implementations, the locking member includes a pair of spring arms.

The spring arms can include protrusions.

The locking member can include finger tabs for displacing the spring arms to a disengaged position.

In some implementations, the cup body is pivotably connected to the sleeve.

In certain implementations, the sleeve includes a proximal end portion and a distal end portion pivotably attached to the proximal end portion.

In some implementations, the locking member includes a cantilever arm.

In certain implementations, the locking feature comprises a recess.

In some implementations, the locking feature includes a recess, and the spring arms include protrusions adapted to engage the recess.

In certain implementations, the locking member includes finger tabs operable to disengage the protrusions from the recess.

In certain implementations, the manipulator handle includes an elongate frame and a tip hub. The elongate frame has a proximal end portion and a distal end portion. The distal end portion is configured to be inserted into a vagina. The tip hub is configured to releasably receive and support a manipulator tip. The tip hub is pivotally connected to the distal end portion of the frame.

In some implementations, the manipulator handle also includes a grip pivotally connected to the proximal end portion of the frame. The grip is moveable relative to the frame to control relative movements of the tip hub.

In certain implementations, the grip is movable relative to the frame to control relative movements of the cup body when the colpotomizer cup is positioned in the locked position on the manipulator handle.

In some implementations, the uterine manipulator includes a manipulator tip, and a cup base of the colpotomizer cup is arranged coaxially with a tip base of the manipulator tip when the colpotomizer cup is positioned in the locked position on the manipulator handle.

In certain implementations, the manipulator handle includes an arcuate shaft.

In some implementations, the colpotomizer cup includes a vaginal occluder.

In certain implementations, the uterine manipulator also includes a manipulator tip mounted to the manipulator handle. The locking member of the colpotomizer cup is configured to engage the locking feature of the uterine manipulator handle for locking the colpotomizer cup in a predetermined position relative to the manipulator tip.

Implementations may provide one or more of the following advantages.

Some implementations provide for placement of a uterine manipulator tip within a uterus prior to placement a colpotomizer cup about the cervix, which can help to provide for placement of the manipulator tip with limited visual obstructions.

Some implementations provide for a colpotomizer cup that locks in a stable position, relative to a manipulator handle, which can help to ensure that the cup does not tip or shift out of position during use.

Some implementations provide for audible and tactile feedback to alert a surgeon that a colpotomizer cup is in a locked position during placement of the colpotomizer cup. In some cases, for example, a surgeon simply slides the colpotomizer cup forward, along a manipulator handle, until it locks into place with no guessing about the position and without having to take additional steps, such as fine adjustment with a thumbscrew.

In some implementations, a simple uterine manipulator design with slidable colpotomizer cup has intuitive operation and requires only minimal training.

In some implementations, a simple uterine manipulator design allows for loading of a colpotomizer cup on a manipulator handle that takes only a few seconds, and then the sliding of the colpotomizer cup along the manipulator handle and into a locked position takes only a few additional seconds with additional assurance of a built-in position locking feature.

Other aspects, features, and advantages are in the description, drawings, and claims.

DESCRIPTION OF DRAWINGS

FIGS. 4B and 4C are left and right side views, respectively, of the manipulator handle FIG. 4A.

FIG. 12A is a perspective view of a colpotomizer cup with a pivotable cup body.

FIG. 15A is a perspective view of a colpotomizer cup with a pivotable cup body and a hinged sleeve.

DETAILED DESCRIPTION

Figure 1:
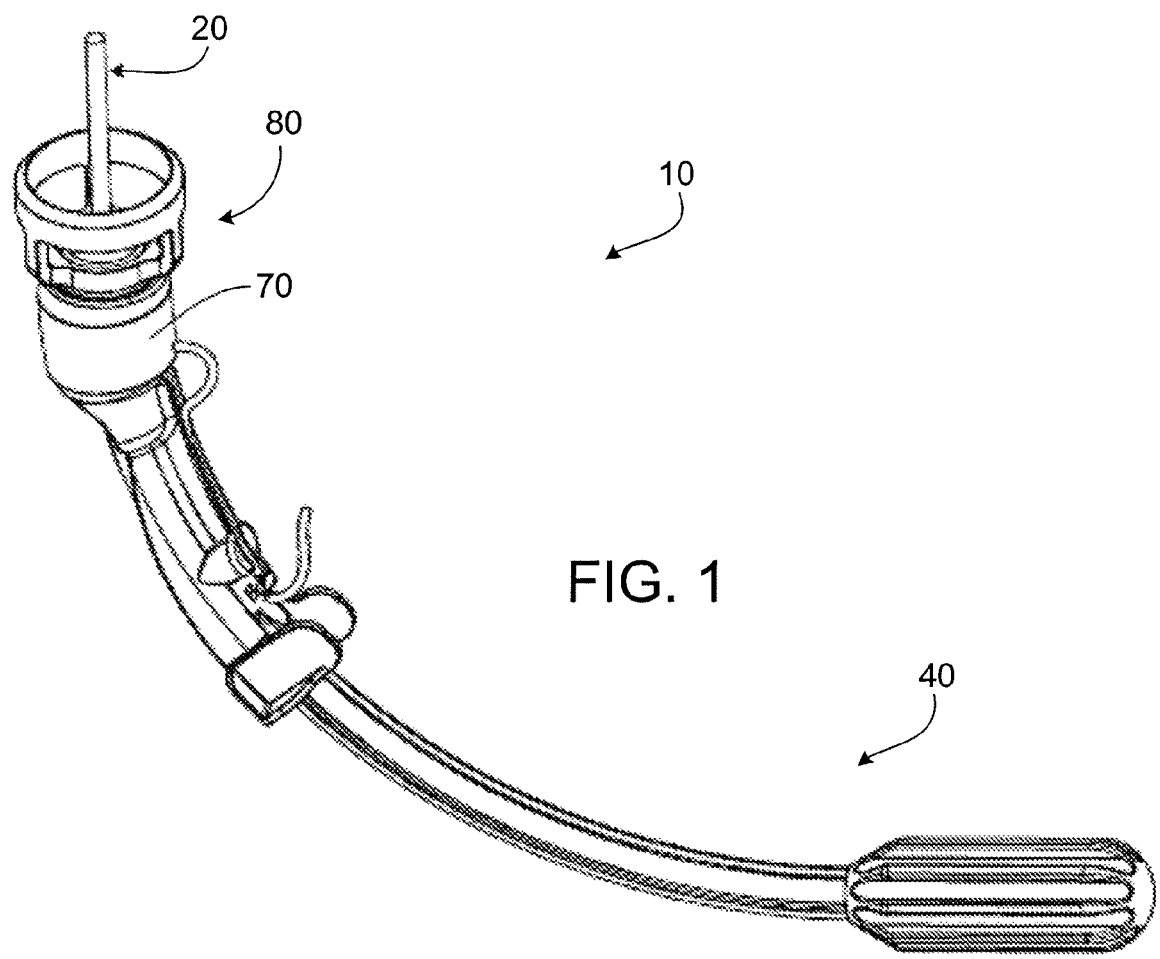
FIG. 1 is a perspective view of a uterine manipulator.

FIG. 1 illustrates a uterine manipulator 10 adapted for insertion into a vaginal cavity for use in female pelvic surgical procedures. The uterine manipulator 10 includes a manipulator tip 20 configured to extend within a cervix, for use in repositioning a uterus, and releasably coupled to a manipulator handle 40. The uterine manipulator 10 also includes a colpotomizer cup 80 that is configured to receive a cervix.

Notably, the colpotomizer cup 80 is displaceable along the length of the manipulator handle 40. The ability to displace the colpotomizer cup 80 can allow for quicker and easier positioning of the manipulator tip 20 within a cervix since this procedure can be performed without the visual obstruction of colpotomizer cup 80. Then, once proper placement of the manipulator tip 20 is visually confirmed, the colpotomizer cup 80 can be advanced along the manipulator handle 40 into engagement with the cervix.

Figure 2A:
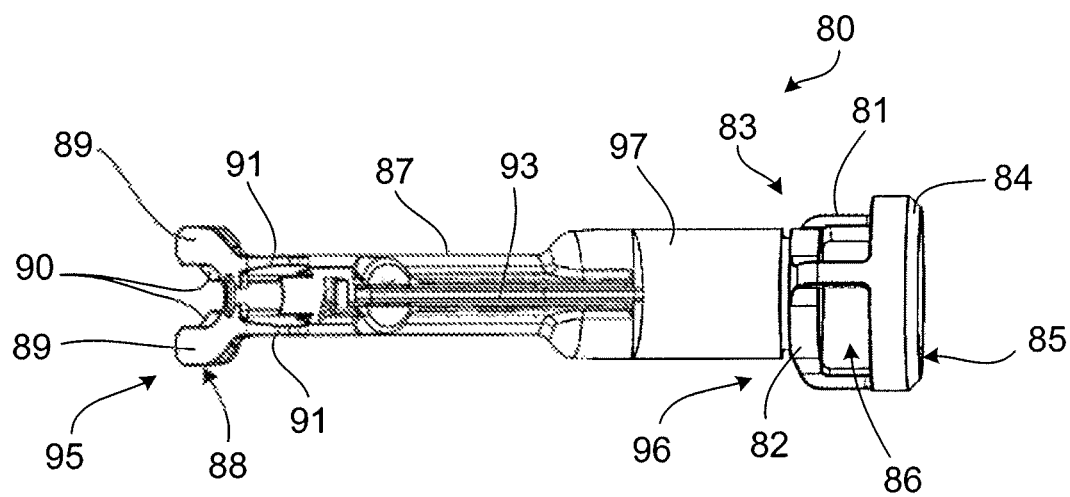
FIG. 2A is a side view of a colpotomizer cup of the uterine manipulator of FIG. 1.
Figure 2B:
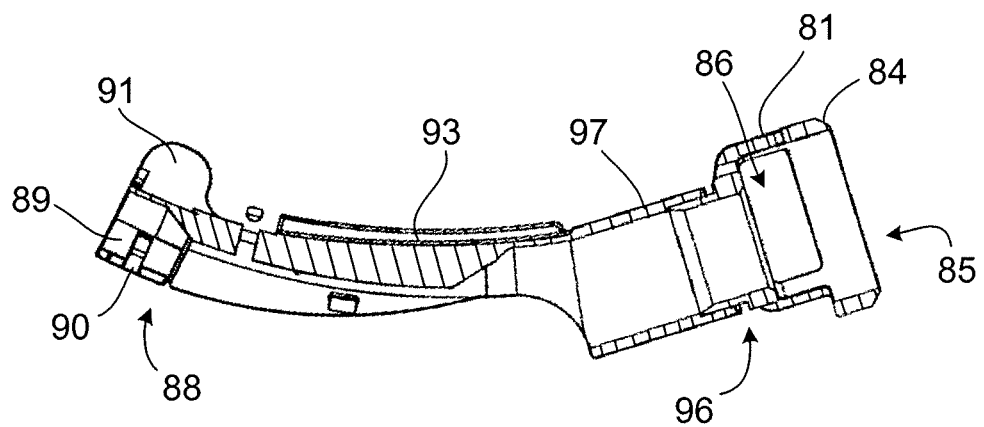
FIG. 2B is a cross-section side view of the colpotomizer cup of FIG. 2A, taken along line 2B-2B.
Figure 2C:
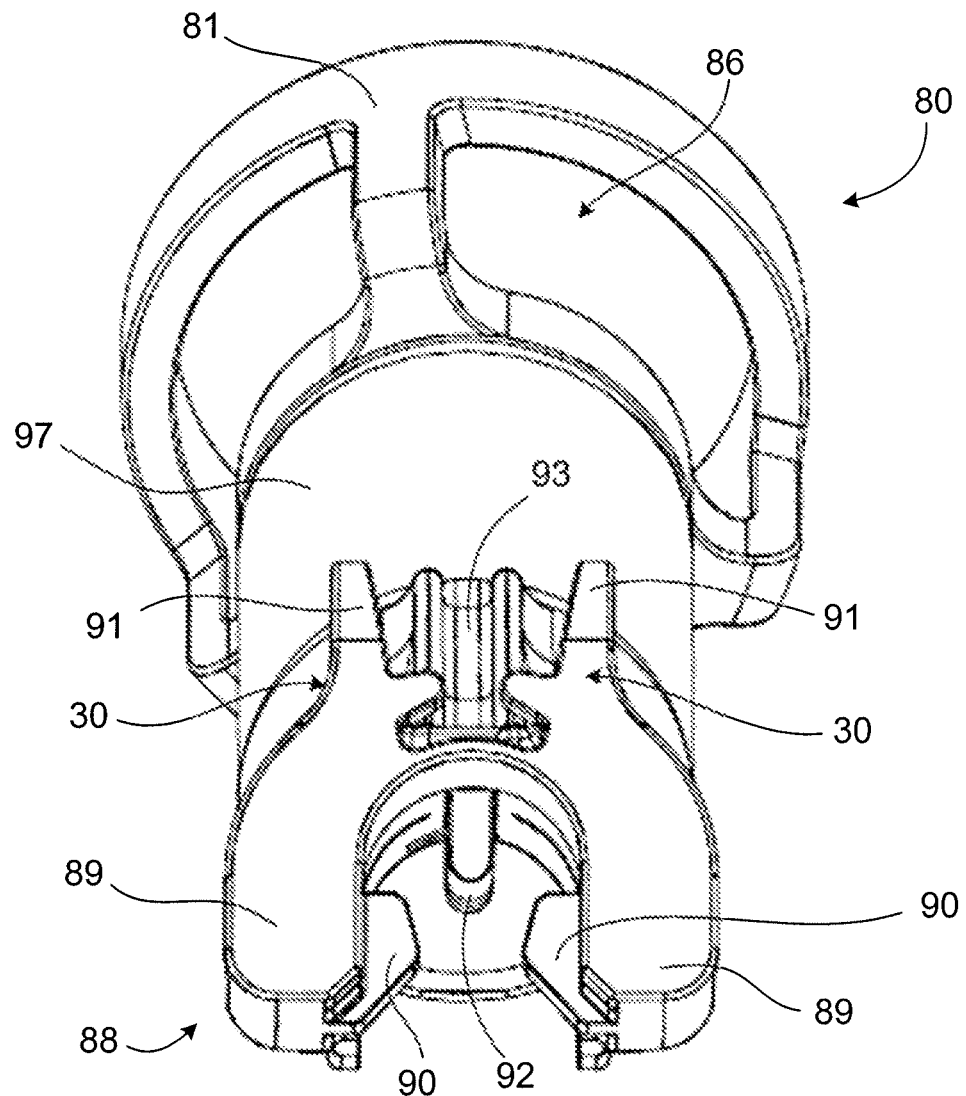
FIG. 2C is an end view of the colpotomizer cup of FIG. 2A.

Referring to FIGS. 2A-2C, the colpotomizer cup 80 includes an annular body 81 ("cup body"), a cup base 82 at a proximal end 83 and a rim 84 at a distal end 85. The rim 84 is beveled to permit anatomical landmark and incision backstop during use. Viewing windows 86 are provided in the annular body 81.

A sleeve 87 extends outwardly from the cup base 82. At its proximal end 95, the sleeve 82 includes a locking member 88. The locking member 88 consists of a pair of spring arms 89 each including a protrusion 90. The protrusions 90 are configured (e.g., sized and shaped) to slide within side slots 48 (FIG. 5) and also to engage a mating recess 41 (FIG. 5) in the manipulator handle 40, for locking the colpotomizer cup 80 at a predetermined position along the length of the manipulator handle 40. The spring arms 89 include finger tabs 91 that can be engaged (e.g., pressed as indicated by arrows 30, FIG. 3) to release (disengage) the locking member 88. The colpotomizer cup 80 also includes a protuberance 92, which is adapted to engage with and slide within a top slot 49 (FIG. 4A) in the manipulator handle 40. The colpotomizer cup 80 also includes a valley 93 for receiving and holding catheter tubing.

The colpotomizer cup 80 is formed of material suitable for medical devices, that is, medical grade material. Plastics, such as polyvinylchloride, polycarbonate, polyolefins, polyproylene, polyethylene, or other suitable medical grade plastics, or metals, such as stainless steel or aluminum, can be used.

In some implementations, the annular body 81 ("cup body") and the sleeve 87 are formed (e.g., molded) as separate items that can then be connected together (e.g., via press fit or snap fit). This two-piece assembly can allow annular bodies of different sizes (e.g., different diameters) to be used with the same sleeve.

Figure 3:
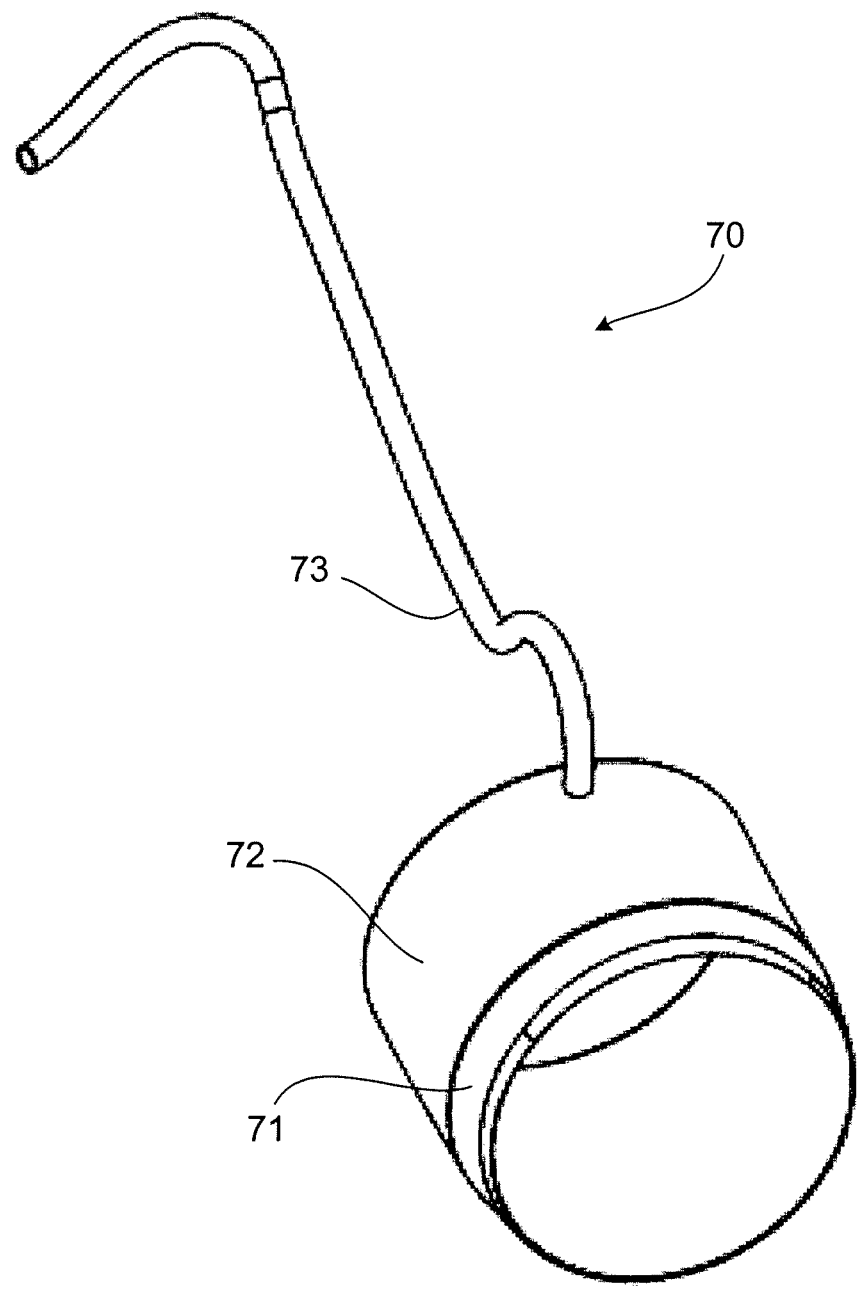
FIG. 3 is a perspective view of a vaginal occluder of the uterine manipulator of FIG. 1.
Figure 4A:
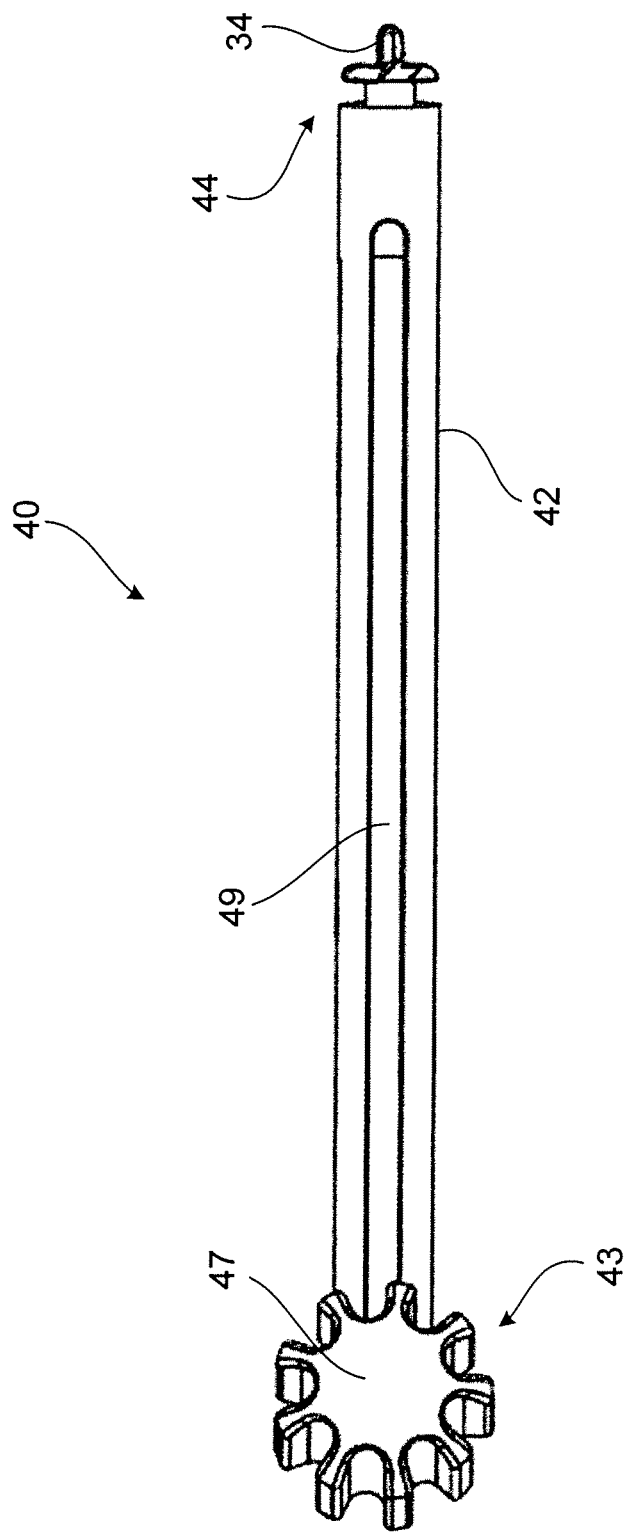
FIG. 4A is a top view of a manipulator handle of the uterine manipulator of FIG. 1.
Figure 4B:
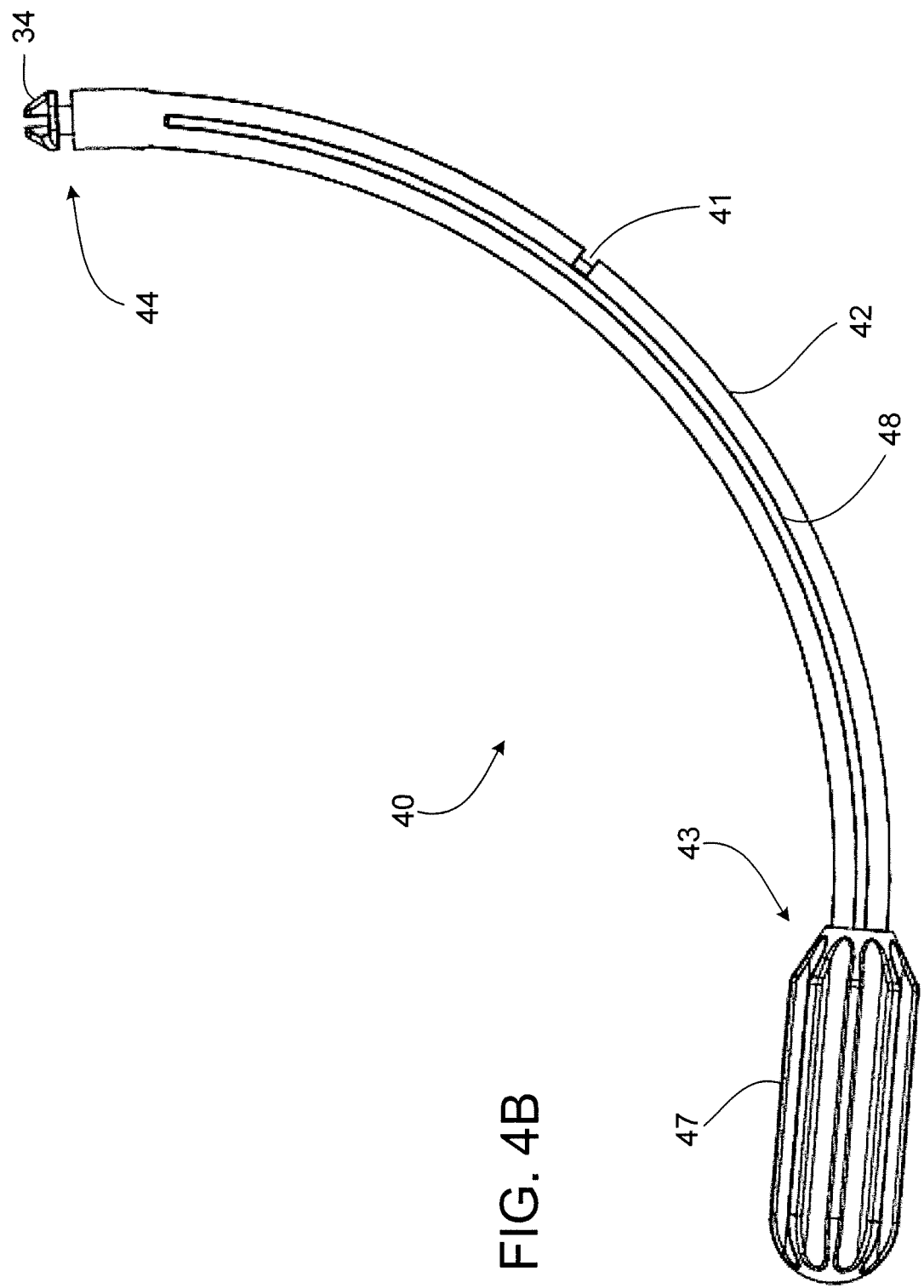

At its distal end 96 the sleeve 87 includes a collar 97 that supports a vaginal occluder 70. Referring to FIG. 3, the vaginal occluder 70 includes a main body 71, which can be mounted concentrically about the collar 97, an expandable balloon cuff 72, and a balloon cuff catheter tube 73. The balloon cuff catheter tube 73 is affixed to the balloon cuff 72 and communicates fluid to the balloon cuff 72 when inflation is desired. When assembled with the colpotomizer cup 80, the balloon cuff catheter tube 73 is received within the valley 93. The vaginal occluder 70 can be constructed of a medical grade silicone suitable for injection molding.

As shown in FIGS. 4A-4D, the manipulator handle 40 includes an elongate, arcuate shaft 42 having a proximal end portion 43 and a distal end portion 44. A recess 41 is disposed along an outer surface 39 of the shaft 42. A grip 47 is coupled to the proximal end portion 43 of the shaft 42. The grip 47 can be integrally formed with the shaft 42 or can be a separate piece (e.g., a removable piece). The manipulator handle 40 also includes a tip hub 34 disposed at the distal end portion 44. The tip hub 34 is configured to releasably receive and support the manipulator tip 20.

Figure 4D:
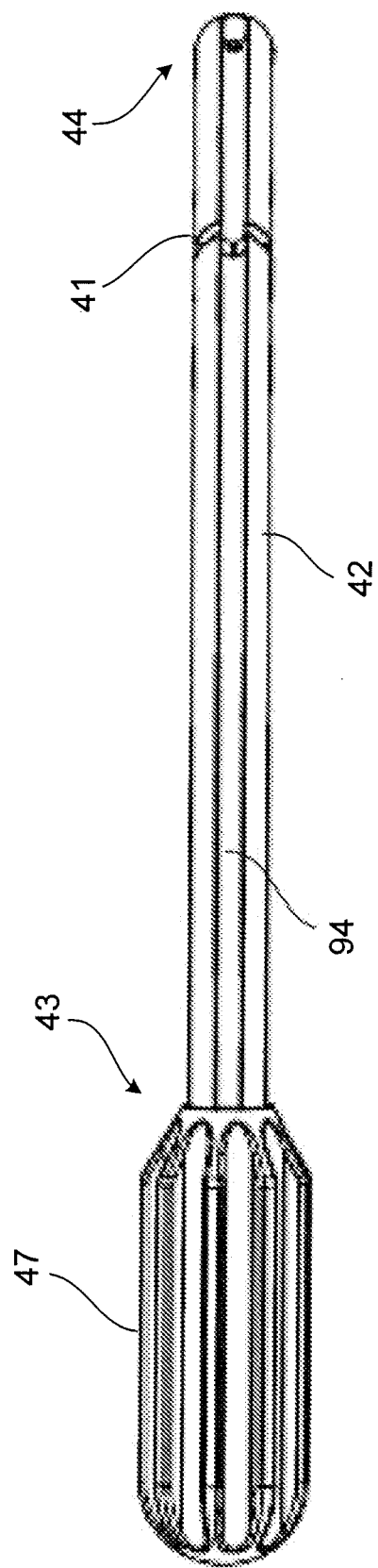
FIG. 4D is a bottom view of the manipulator handle of FIG. 4A.

A top slot 49 (FIG. 4A), and side slots 48 (FIGS. 4B and 4C) extend along the top and sides of the manipulator handle 40. The protuberance 92 and protrusions 90 of the sleeve 87 engage and slide within the top slot 49 and side slots 48, respectively, to inhibit rotation of the colpotomizer cup 80 relative to the shaft 42, e.g., as the colpotomizer cup 80 is displaced (slid) along the length of the shaft 42. Referring to FIG. 4D, a channel 94 is provided along the bottom of the shaft 42 for receiving and holding catheter tubing (e.g., a catheter tube 24 of the manipulator tip 20).

The various components of the manipulator handle 40, including the shaft 42, the grip 47 and the tip hub 34 can be formed, e.g., molded and/or machined, from materials that are biocompatible and capable of withstanding medical device sterilization procedures, such as by heat-based methods (e.g., autoclave, steam autoclave, or dry heat oven). Suitable materials that are capable of withstanding medical device sterilization procedures include metals, such as stainless steel and aluminum, and polymers, such as Polyoxymethylene (POM) commonly known under the DuPont™ brand name Delrin®.

Figure 5:
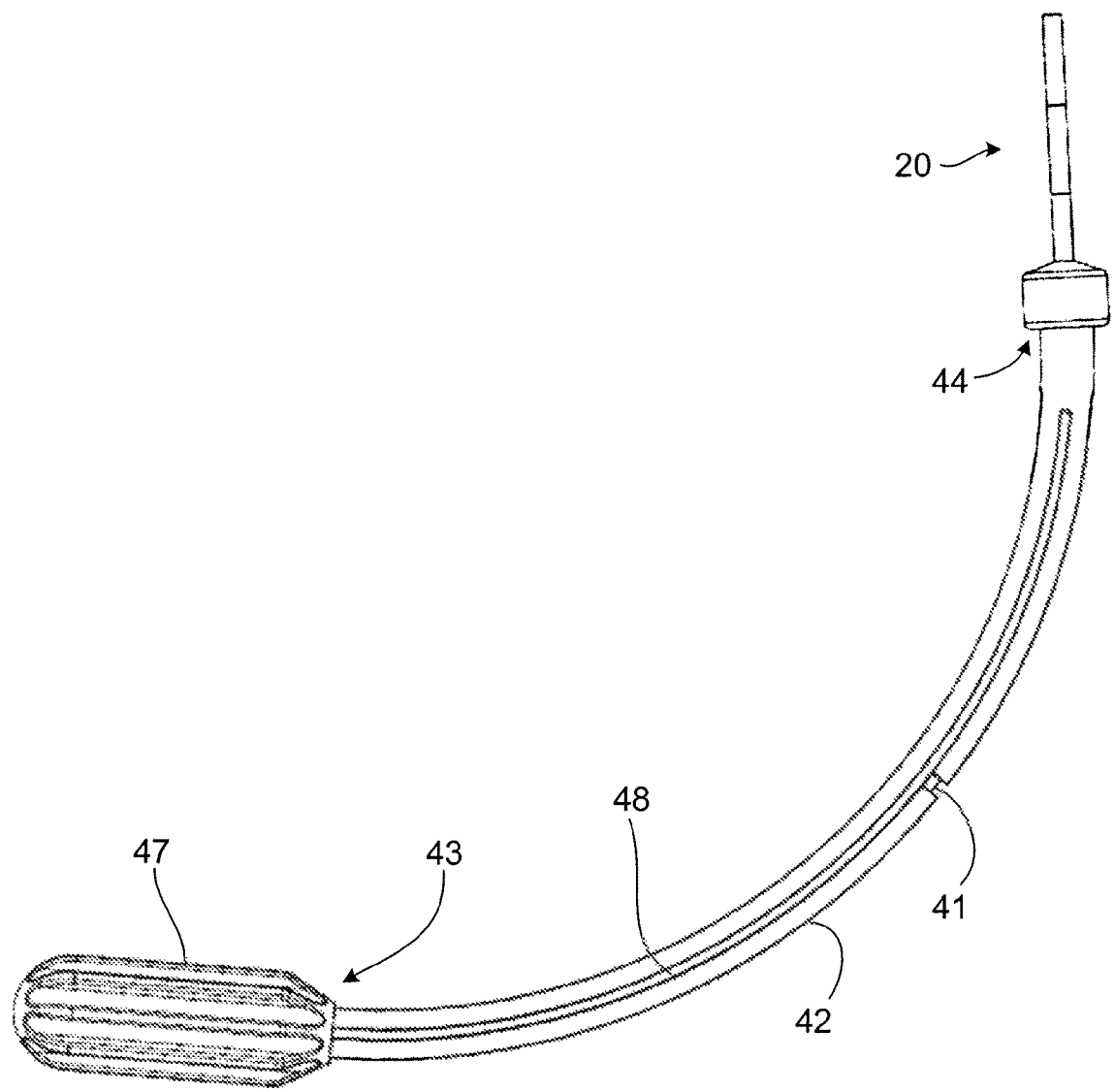
FIG. 5 is a side view of the manipulator handle of FIG. 4 with a manipulator tip.
Figure 6:
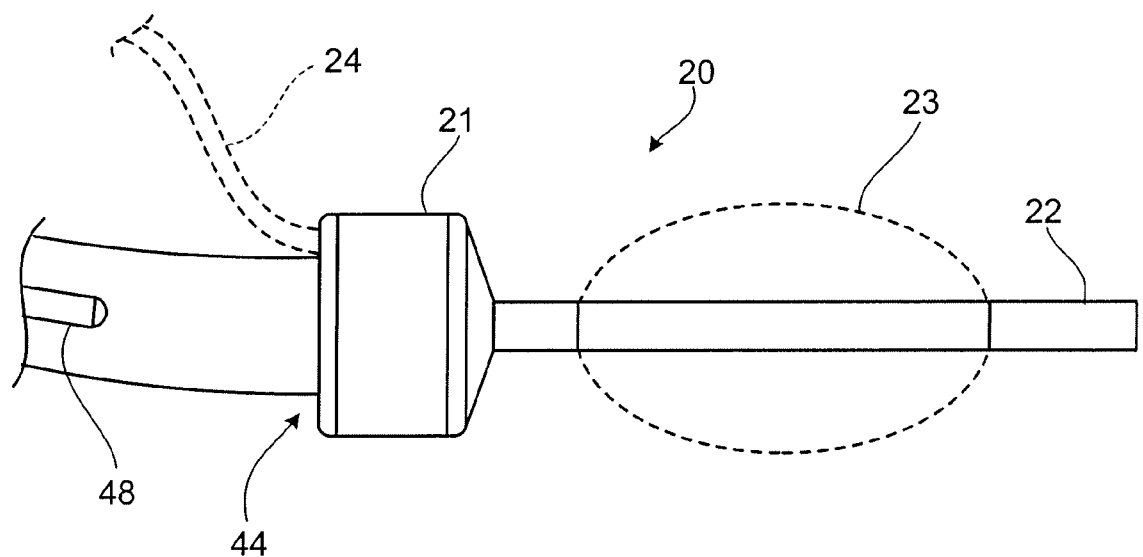
FIG. 6 is a detailed view of the manipulator tip from FIG. 5.

Referring to FIGS. 5 and 6, the manipulator tip 20 is mounted to the distal end portion 44 of the shaft 42. As shown in FIG. 6, the manipulator tip 20 includes a tip base 21, which mates with the tip hub 34 of the manipulator handle 40, and a finger 22 that extends from a first surface of the tip base 21. The finger 22 is configured (e.g., sized and shaped) for insertion into a cervix. The finger 22 carries an expandable balloon 23. A catheter tube 24, extending from the tip base 21, is in fluid communication with the expandable balloon 23, for inflating the expandable balloon 23. When the manipulator tip 20 is assembled with the manipulator handle 40 the catheter tube 24 is retained within the channel 94 along the bottom of the shaft 42. Suitable manipulator tips are commercially available from CooperSurgical, Trumball, Conn., under the RUMI® tips mark, such as CooperSurgical item numbers UMW676, UMB678, UMG670, and UML516.

Figure 7A:
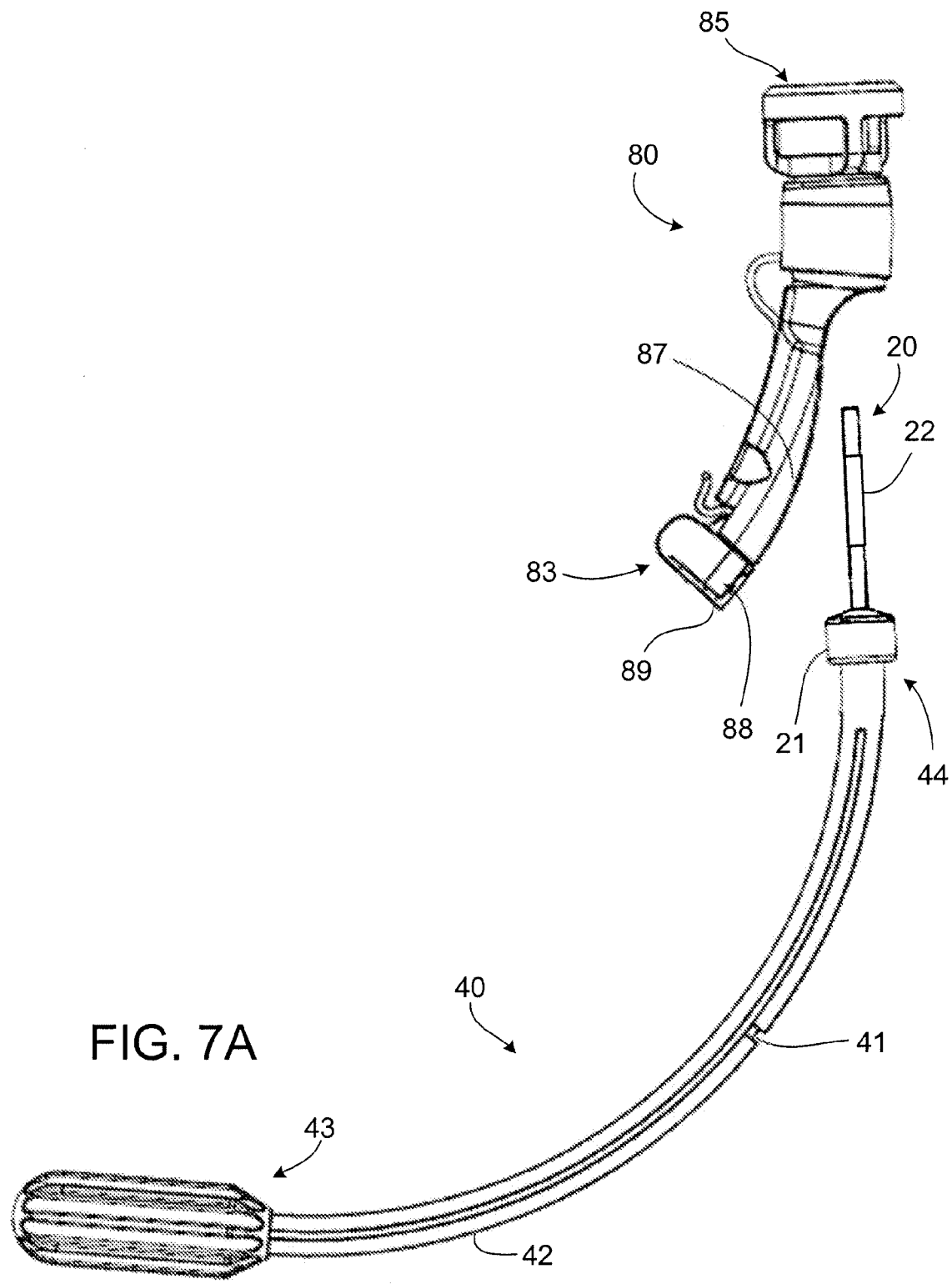
FIGS. 7A-7C illustrate assembly of the colpotomizer cup of FIG. 2A onto the manipulator handle of FIG. 5.
Figure 7B:
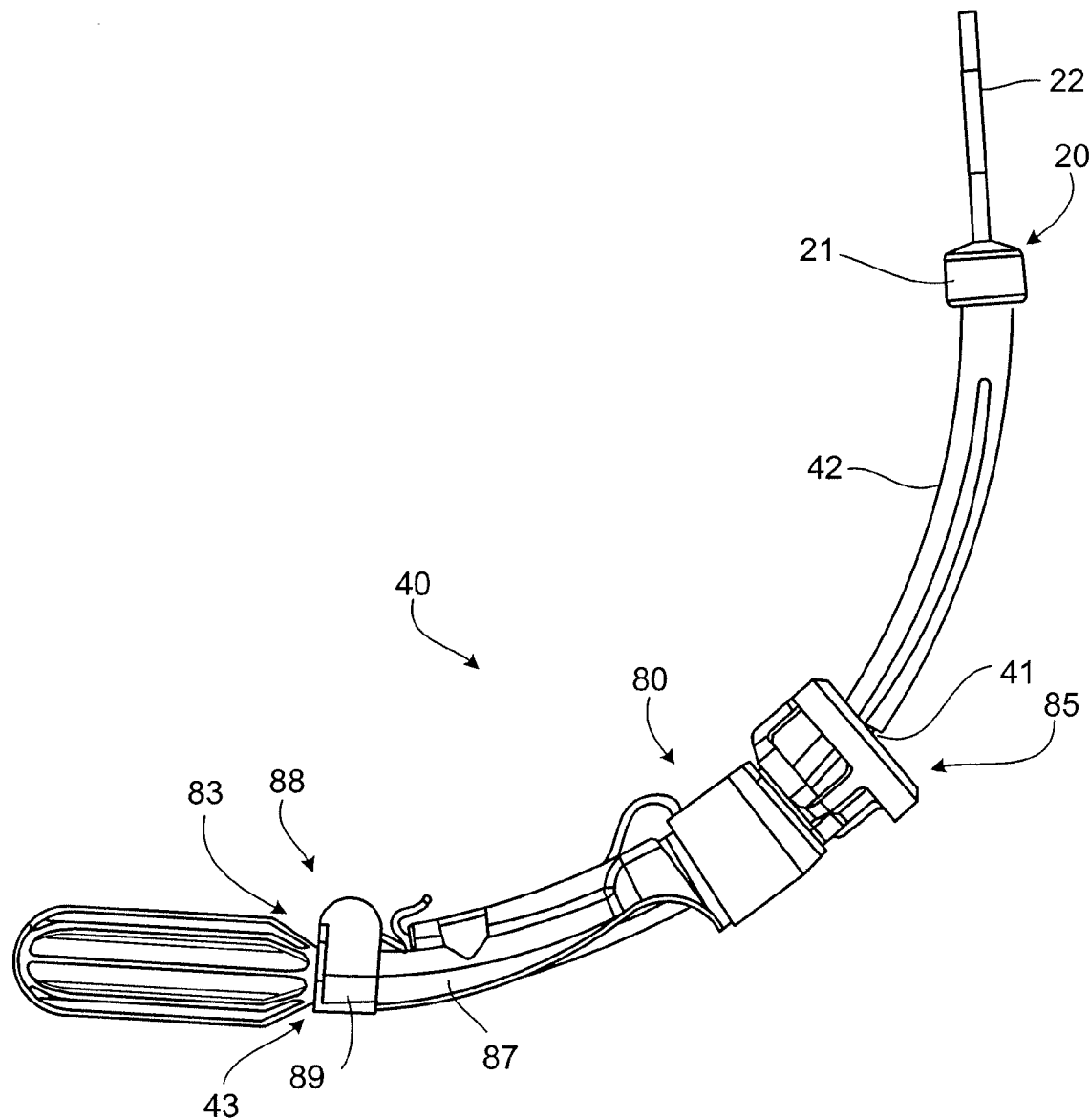
Figure 7C:
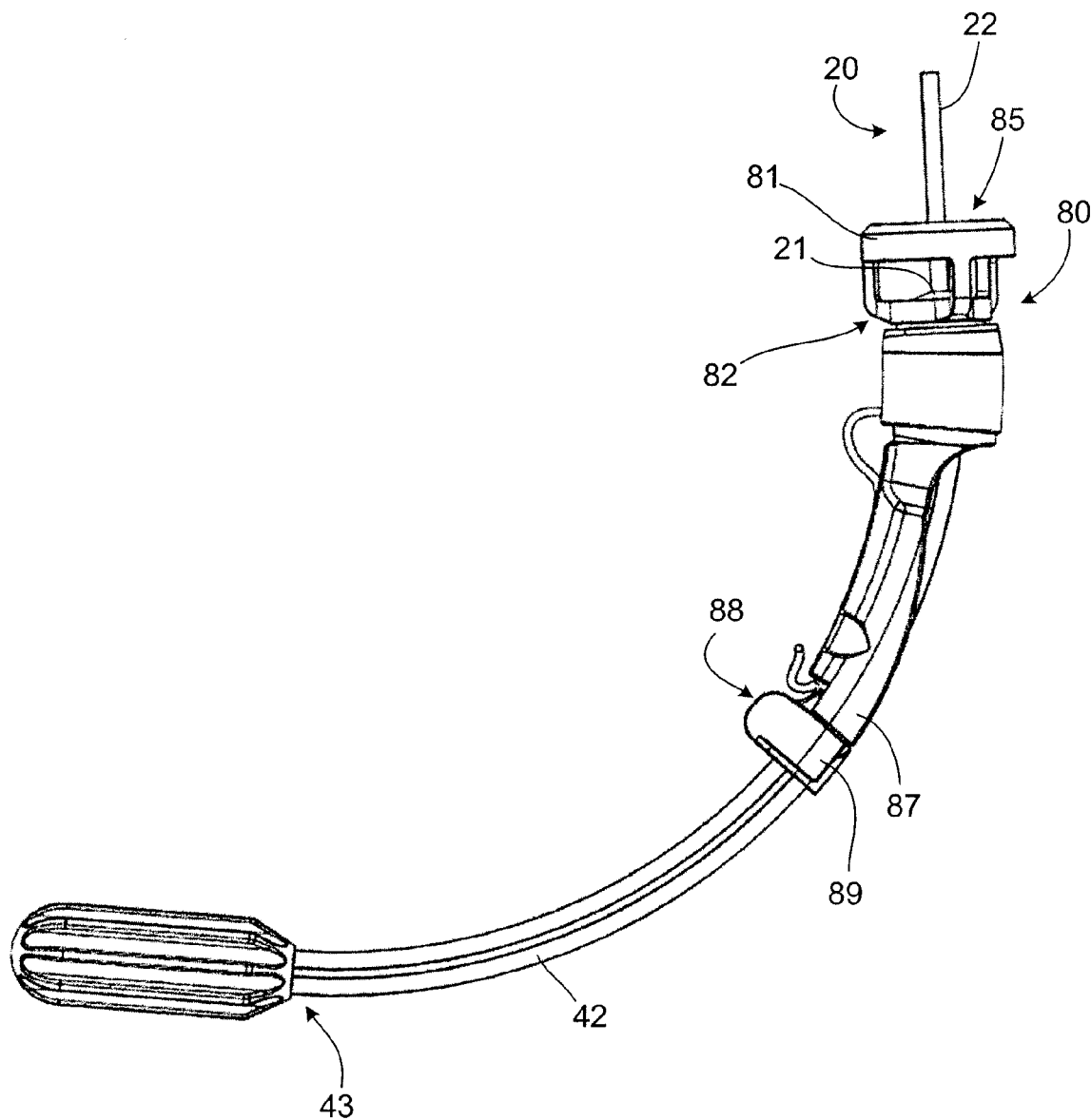

Referring to FIGS. 7A-7C, the colpotomizer cup 80 is loaded onto the manipulator handle 40 by advancing the colpotomizer cup 80 over manipulation tip 20 at the distal end portion 44 of the shaft 44, with the manipulator tip 20 passing through the proximal and distal ends 83, 85 of the colpotomizer cup 80 (as illustrated in FIG. 7A) as the colpotomizer cup 80 is slid back towards the proximal end portion 43 of the shaft 42. Once the locking member 88 is advanced along the shaft 42 to a point beyond the recess 41 the spring arms 89 are forced over the shaft 42 near the proximal end portion 43 and into a loaded position, as illustrated in FIG. 7B. As shown in FIG. 7B, the sleeve 87 generally conforms to the arcuate shape of the shaft 42. The colpotomizer cup 80 can then be pushed along the shaft 42 towards the distal end portion 44 to a locked position in which the protrusions 90 (FIG. 2C) on the spring arms 89 engage the recess 41 in the shaft 42. As shown in FIG. 7C, in the locked position, the cup base 82 of the colpotomizer cup 80 circumferentially surrounds the tip base 21, of the manipulator tip 20, and the finger 22 extends outwardly through the distal end 85 of the annular body 81.

Methods of Use

The uterine manipulator 10 may be used in a number of procedures that require manipulation of the uterus, including surgical procedures, such as hysterectomies. In one example, the uterine manipulator 10 is used in a total laparoscopic hysterectomy (TLH) surgery. A patient is prepared for TLH surgery according to know procedures. Once prepared, the patient's peritoneal cavity 102 is inflated with a gas (e.g., $CO_2$) to facilitate accessibility and visibility of the female pelvic organs, and surgical instruments, including a laparoscope 152, are inserted through the abdominal wall 104 into the peritoneal cavity 102, see, e.g., FIG. 8.

Figure 8:
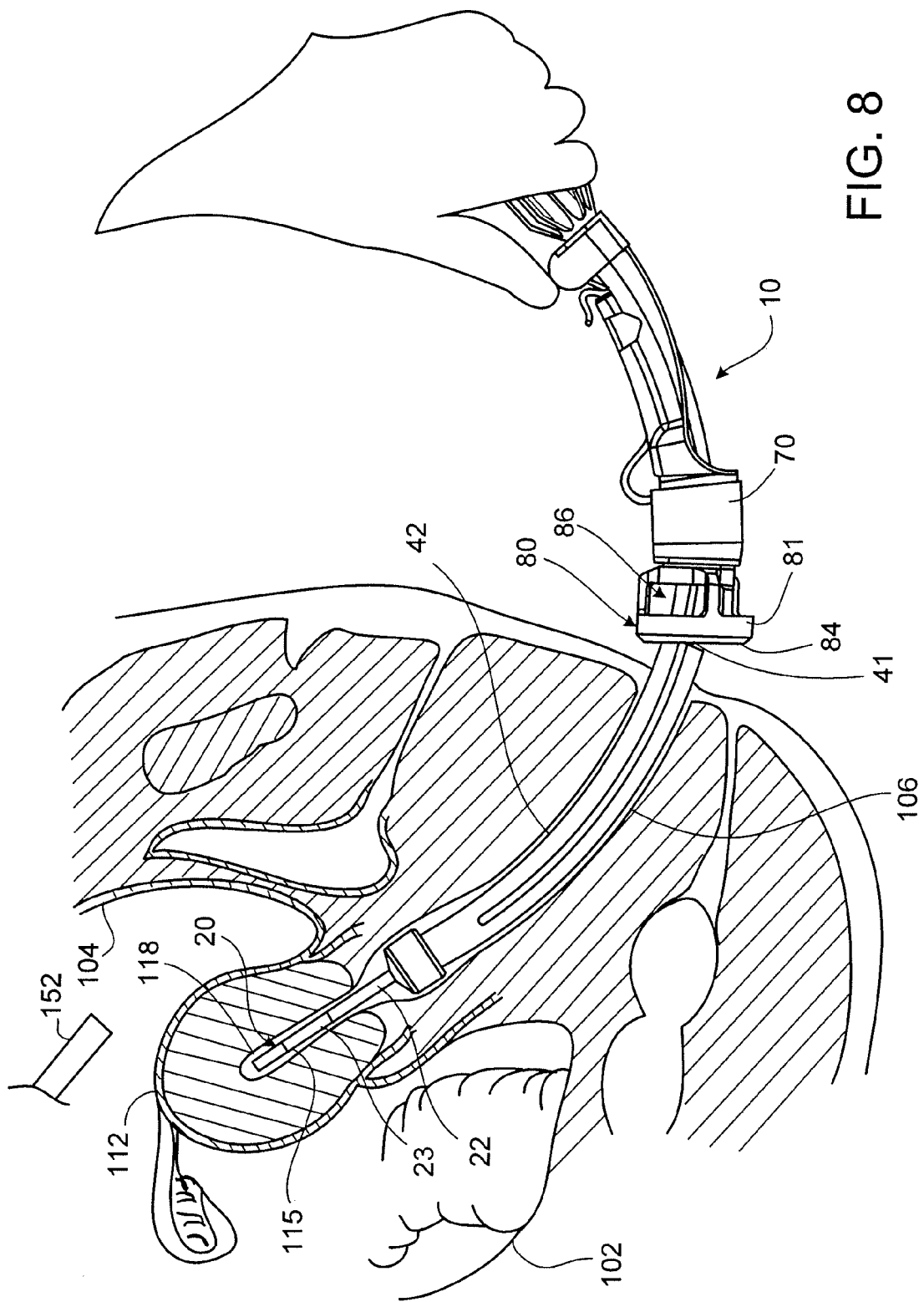
FIG. 8 is a cross-sectional side view of a pelvic cavity showing a fully inserted manipulator tip and a colpotomizer cup in a loaded position on a manipulator handle.
Figure 9:
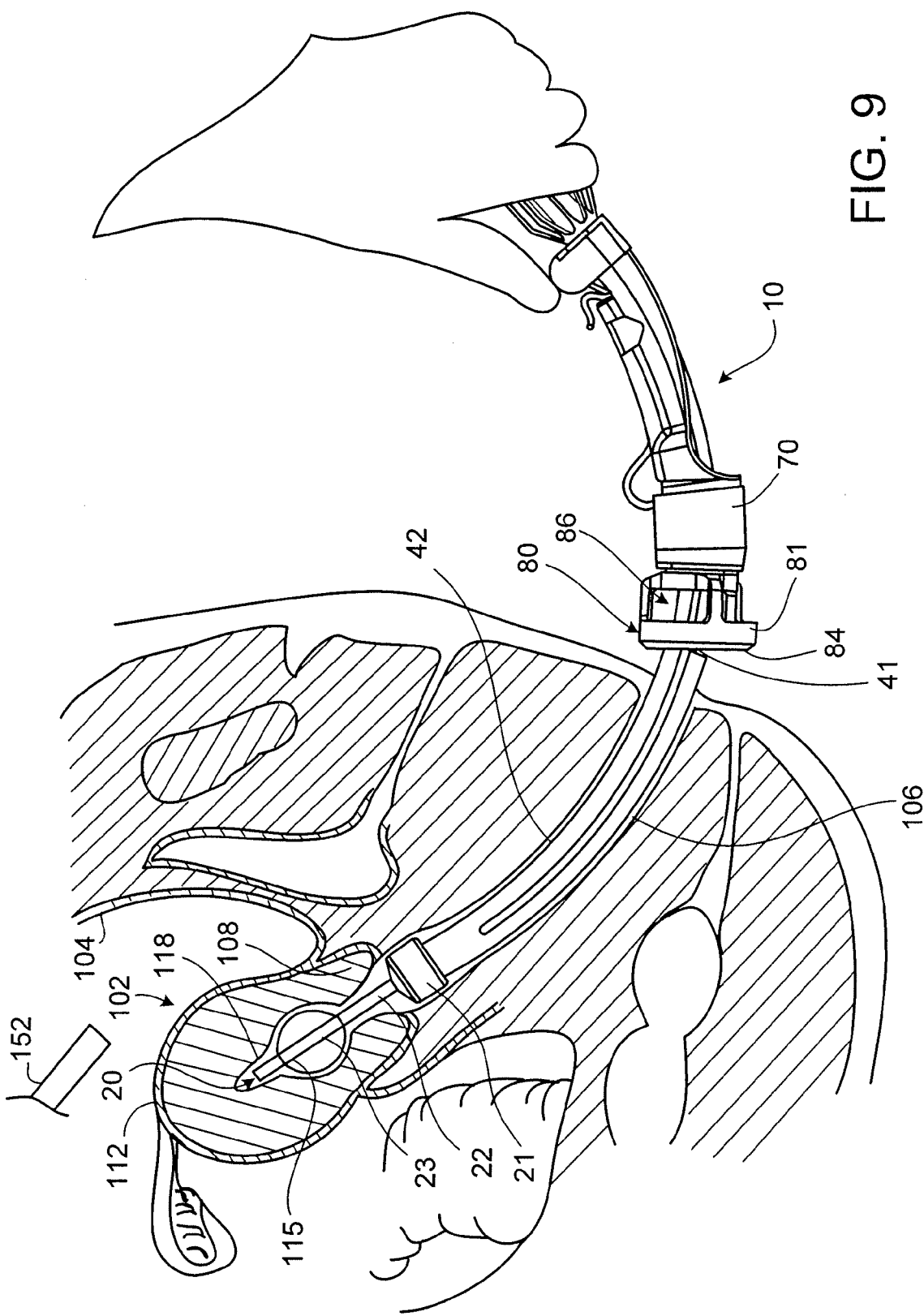
FIG. 9 is a cross-sectional side view of a pelvic cavity showing a fully inserted manipulator tip with an inflated balloon and a colpotomizer cup in a loaded position on a manipulator handle.
Figure 10:
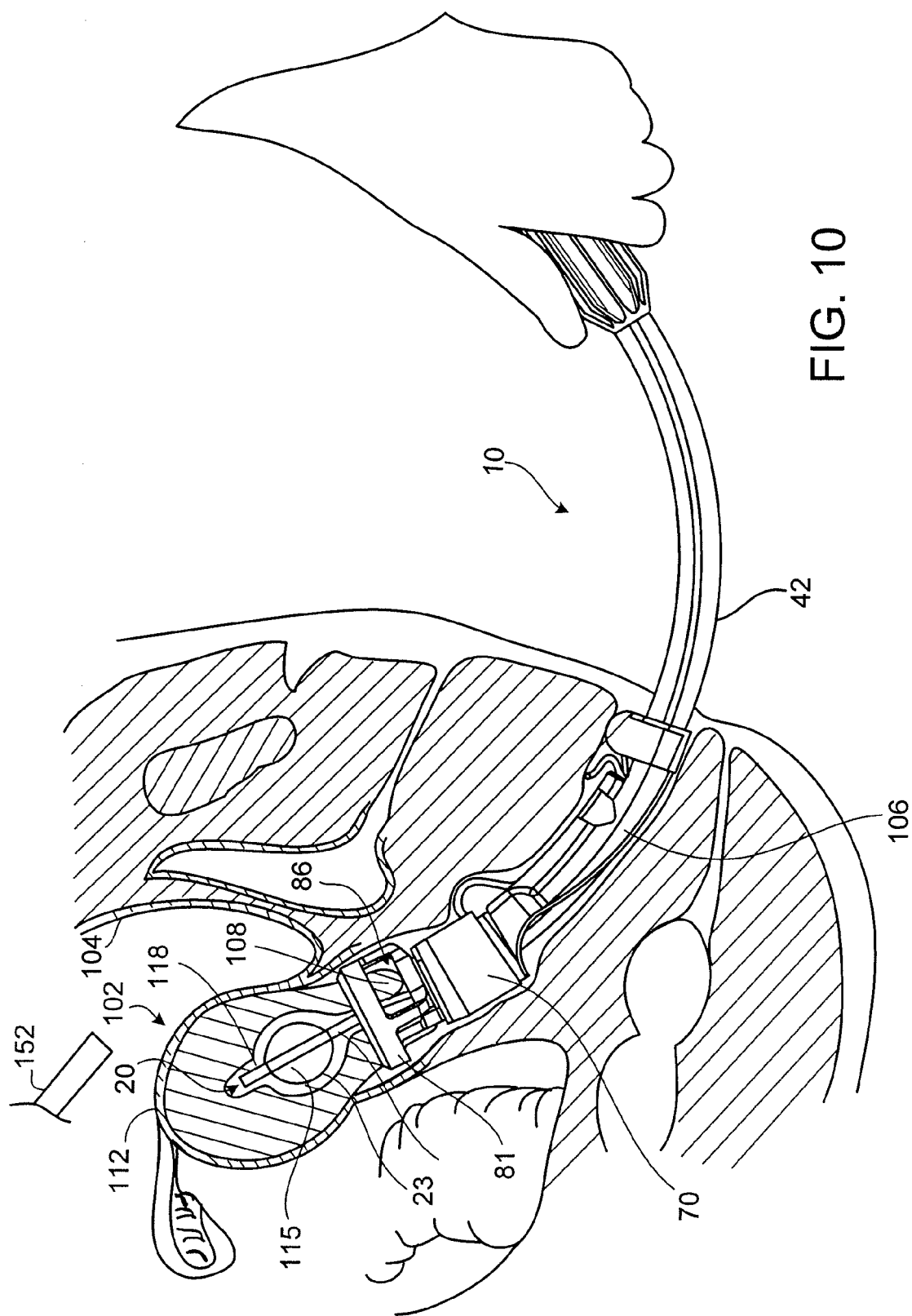
FIG. 10 is a cross-sectional side view of a pelvic cavity showing a fully inserted manipulator tip and a colpotomizer cup in a locked position on a manipulator handle.

Next, the uterine manipulator 10, with the colpotomizer cup 80 in the loaded position, is inserted into the vaginal cavity 106, as shown in FIG. 8. When inserted, the finger 22 of the manipulator tip 20 is inserted into the uterus 112 such that a top surface of the tip base 21 abuts the cervix 108 and the balloon 23 is inflated to come into engaging relationship with the uterus interior surface, as shown in FIG. 9. Leaving the colpotomizer cup 80 in the loaded position during insertion of the uterine manipulator 20 can allow for a relatively unobstructed view of the cervix 108 to help ensure proper placement of the manipulator tip 20. After the manipulator tip 20 is properly positioned and the balloon 23 is deployed (e.g., inflated by delivering fluid to the balloon 23 via the catheter tube 24), the colpotomizer cup 80 is advanced from the loaded position toward the locked position, placing the cervix at the base of the colpotomizer cup 80 with the cervix resting against a top surface the tip base 21, as shown in FIG. 10. When locked, the engagement of the protrusions 90 (FIG. 2C) with the recess 41 provides an audible and tactile feedback that will alert the surgeon that the colpotomizer cup 80 is in position and locked. Furthermore, the windows 86 in the colpotomizer cup 80 can provide for visual confirmation of placement. This predetermined locked position helps to ensure that the colpotomizer cup is fully forward in the desired position relative to the manipulator tip 20 and the cervix 108, and the locking engagement between the protrusions 90 on the colpotomizer cup 80 and the recess 41 on the shaft 42 help to ensure that the colpotomizer cup 80 will not tip or shift out of position. In the locked position, the cervix 108 is received into the annular body 81 of the colpotomizer cup 80 and the rim 84 is placed in engaging relationship with the apex 109 of the fornix 110. In this position, the colpotomizer cup 80 provides an anatomical landmark at the base of the uterus 112 (i.e., where the cut needs to be made).

Figure 11:
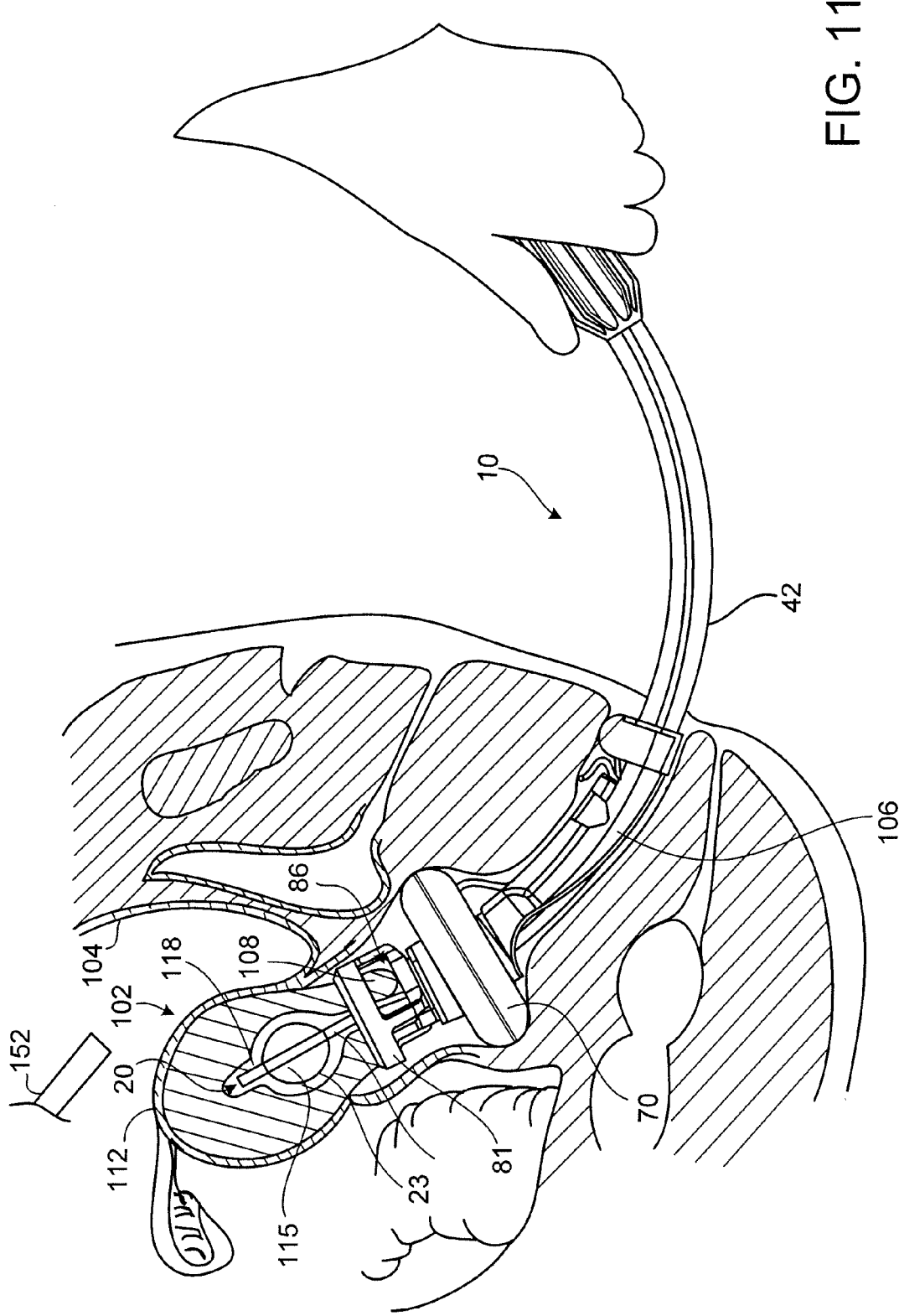
FIG. 11 is a cross-sectional side view of a pelvic cavity showing a uterine manipulator holding a uterus.

Once the colpotomizer cup 80 is arranged in the locked position, the vaginal occluder 70 can be inflated (e.g., with sterile, water-based fluid) to seal the distal vaginal cavity 105, as shown in FIG. 11. The vaginal occluder 70 inhibits, e.g., prevents, the escape of gas used to inflate the peritoneal cavity 102 during and following the first of any colpotomy incisions.

A surgeon can then manipulate or move the uterus 112 into a desired position to perform surgery to cut around the base of the uterus. After the uterus 112 is completely incised such that the uterus 112 is totally free in the peritoneal cavity 102 and held only by the uterine manipulator 10, then the uterine manipulator 10, and the uterus 112, is removed through the vagina.

Other Implementations

While certain implementations have been described above, other implementations are possible.

Figure 12B:
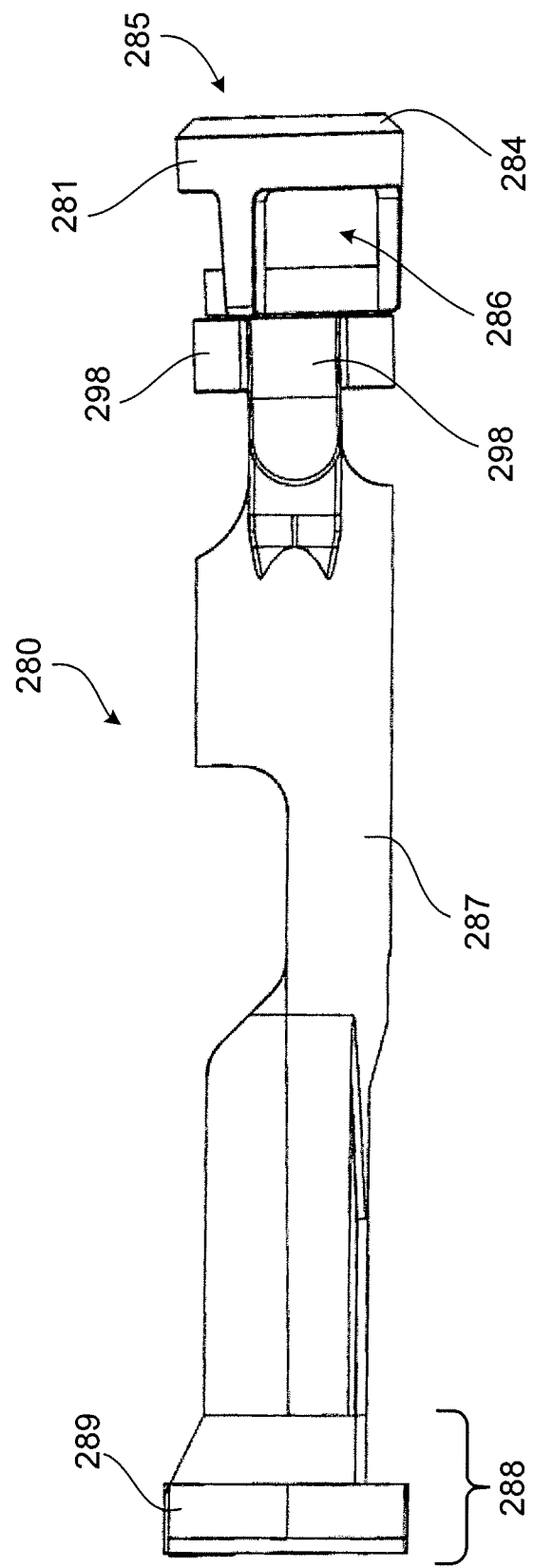
FIG. 12B is a side view of a colpotomizer cup with a pivotable cup body.
Figure 12C:
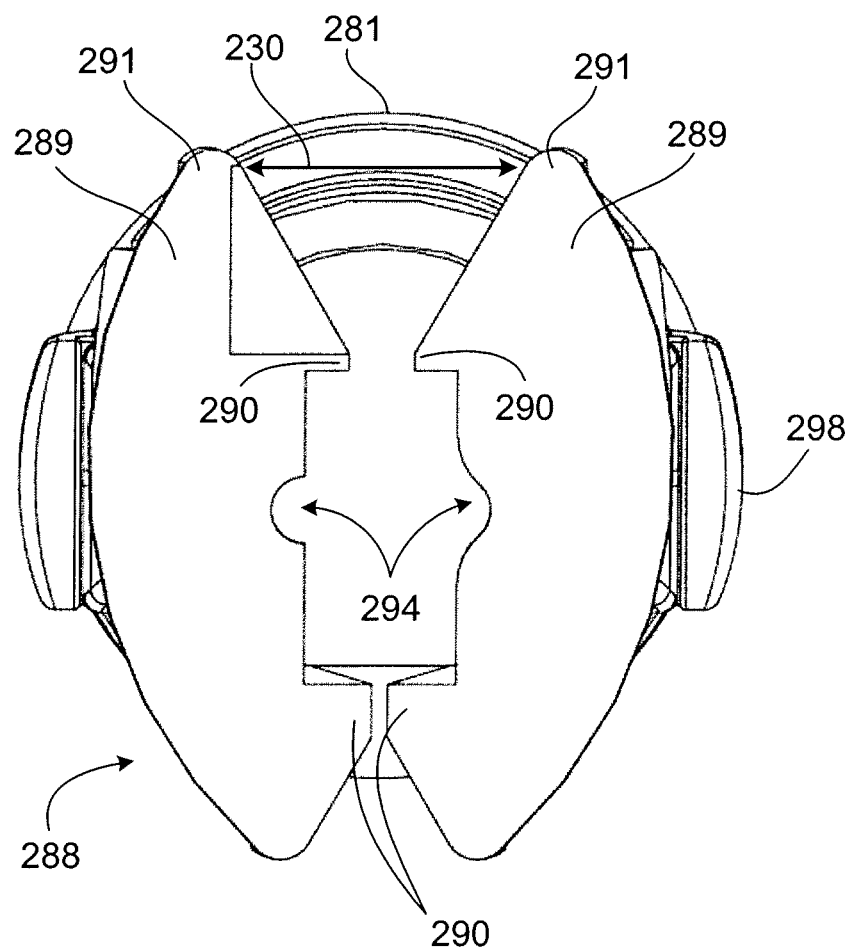
FIG. 12C is an end view of the colpotomizer cup of FIG. 12A.

For example, in another implementation, a colpotomizer cup is configured for use with a uterine manipulator handle having a pivotable tip. FIGS. 12A through 12C illustrate an implementation of a colpotomizer cup 280 that includes an annular body 281 ("cup body"), a cup base 282 at a proximal end 283 and a rim 284 at a distal end 285. The rim 284 is beveled to permit anatomical landmark and incision backstop during use. Viewing windows 286 are provided in the annular body 281.

A sleeve 287 is pivotably connected to the cup base 282 via a hinge adaptor 298. The hinge adaptor 298 allows the annular body 281 to be rotated relative to the sleeve 287, which allows the annular body 281 to move with a pivotable tip 20/tip hub 248 (FIGS. 13A & 13B) of uterine manipulator handle 240. At its proximal end 295, the sleeve 287 includes a locking member 288. The locking member 288 consists of a pair of spring arms 289 each including a protrusion 290. The protrusions 290 are configured (e.g., sized and shaped) to engage a mating recess 241 (FIG. 13A) in the manipulator handle 240, for locking the colpotomizer cup 280 at a predetermined position along the length of the manipulator handle 240. The spring arms 289 also include finger tabs 291 that can be engaged (e.g., pressed as indicated by arrows 230, FIG. 12C) to release (disengage) the locking member 288. As shown in FIG. 12C, the spring arms 289 also include recesses 294, which can accommodate catheter tubing between the sleeve 287 and the uterine manipulator handle 240.

The colpotomizer cup 280 is formed of material suitable for medical devices, that is, medical grade material. Plastics, such as polyvinylchloride, polycarbonate, polyolefins, polyproylene, polyethylene, or other suitable medical grade plastics, or metals, such as stainless steel or aluminum, can be used.

In some implementations, the annular body 281 ("cup body") the sleeve 287, and the hinge adaptor 298 are formed (e.g., molded) as separate items that can then be connected together (e.g., via press fit or snap fit). This three-piece assembly can allow annular bodies of different sizes (e.g., different diameters) to be used with the same sleeve and hinge adaptor.

Figure 13A:
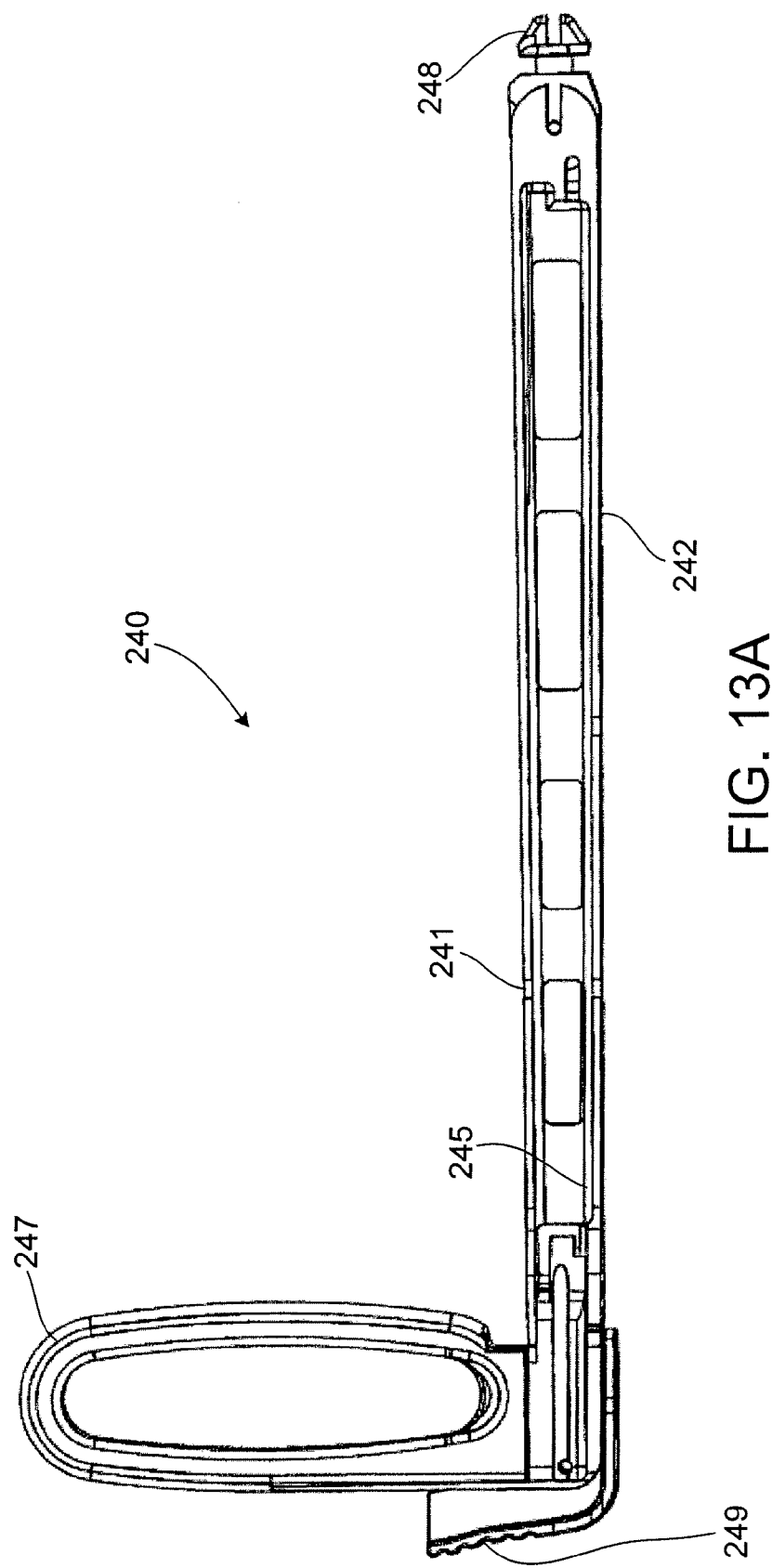
FIG. 13A is a side view of a manipulator handle having an articulable tip hub.

As shown in FIG. 13A, a manipulator handle 240 includes an elongate frame 242, a grip 247, a tip hub 248, and a locking mechanism 249. The grip 247 is affixed in pivotal relationship to a proximal end portion 243 of the frame 242 and the tip hub 248 is affixed in pivotal relationship to a distal end portion 244 of the frame 242. A connecting structure 245 operatively couples the tip hub 248 to the grip 247 such that movement of the grip 247 relative to the frame 242 causes a corresponding movement of the tip hub 248 relative to the frame 242. The connecting structure can, for example, be a wire. The locking mechanism 249 is operable to fix the grip 247 against movement relative to the frame 242. A recess 241 is disposed along a length of the frame 240.

Figure 13B:
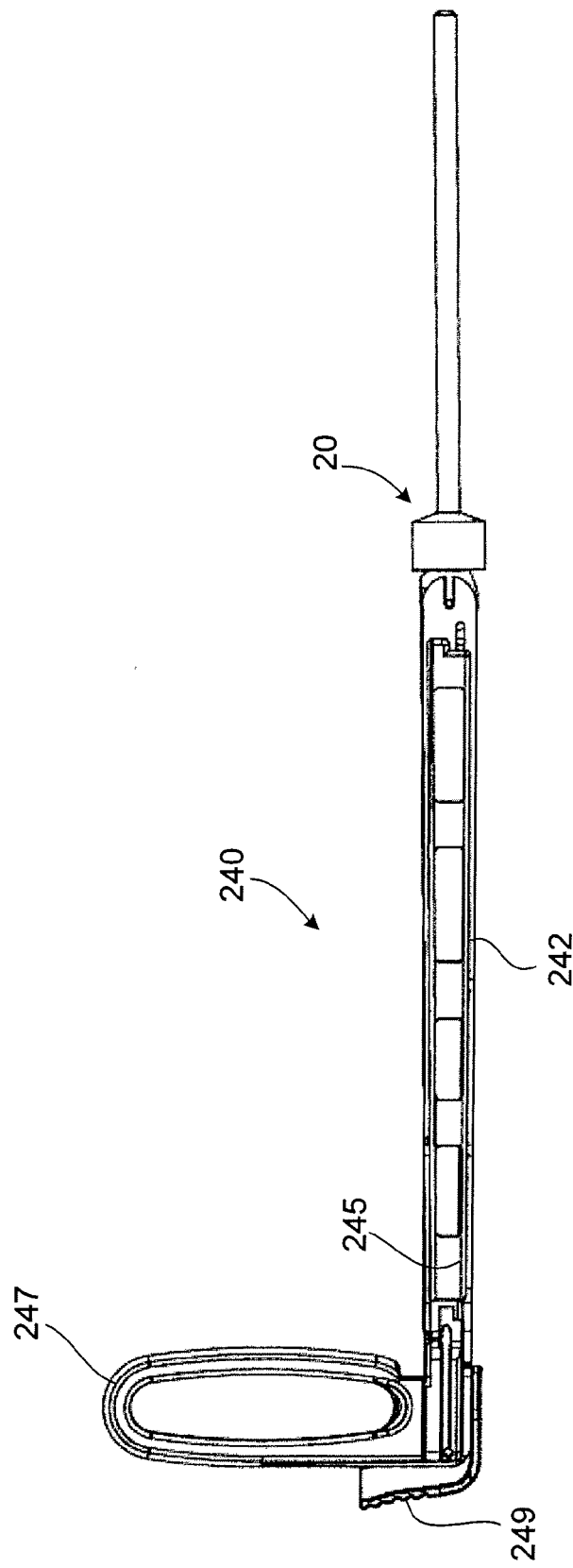
FIG. 13B is a side view of the manipulator handle of FIG. 13A with a manipulator tip mounted thereon.

Referring to FIG. 13B, the tip hub 248 is configured to releasably receive and support a manipulator tip 20.

Figure 14A:
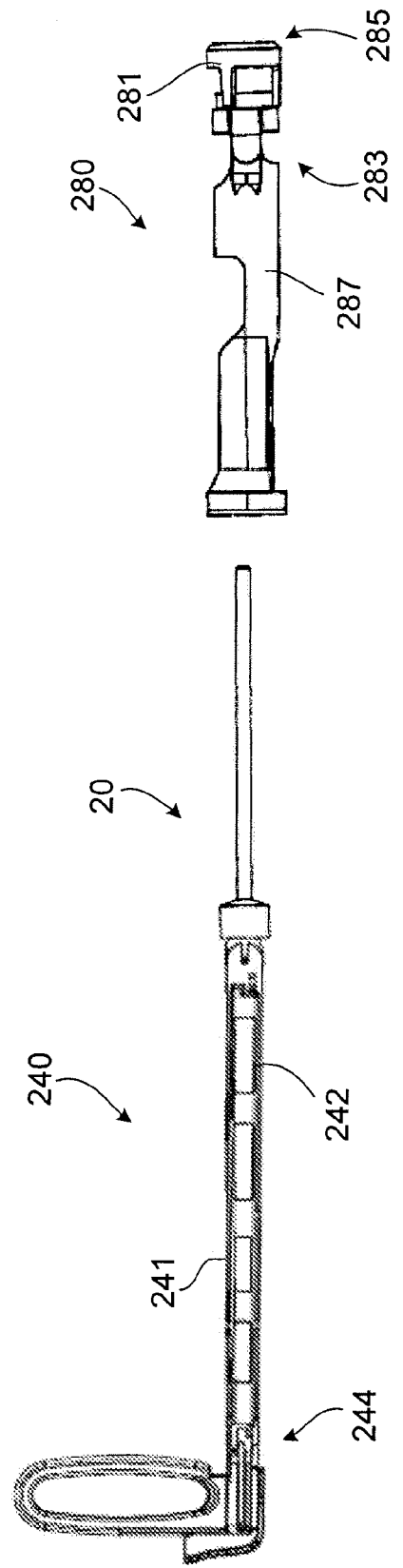
FIGS. 14A-14D illustrate assembly of the colpotomizer cup of FIG. 12A onto the manipulator handle of FIG. 13A.
Figure 14B:
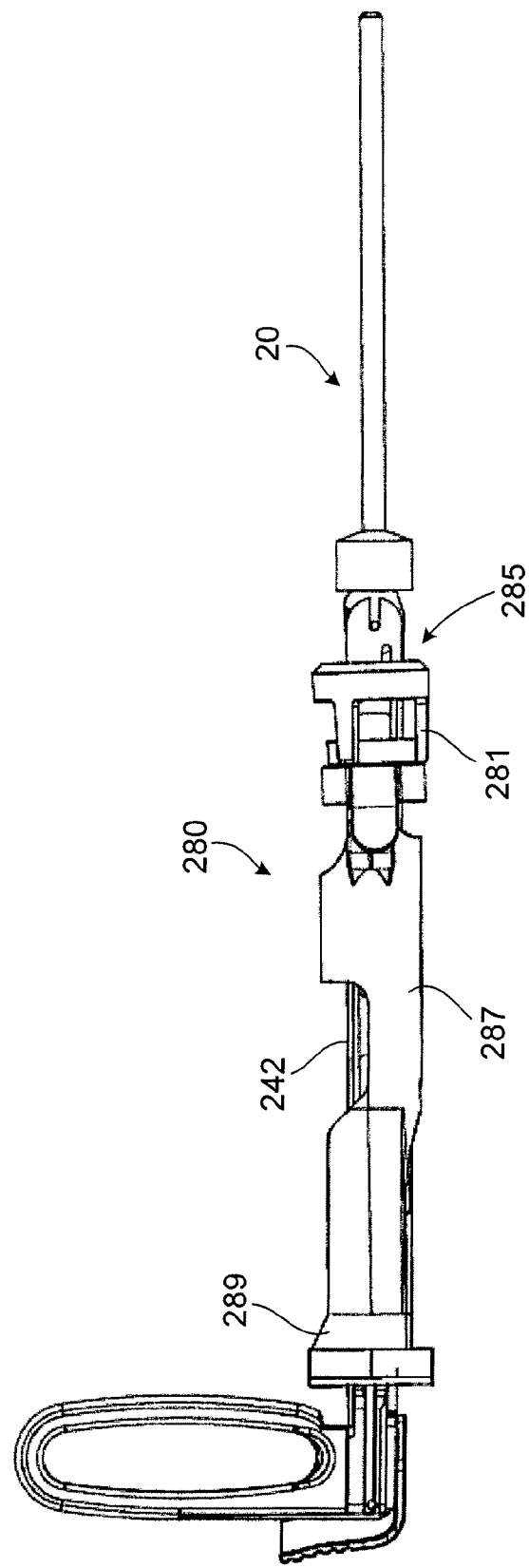
Figure 14C:
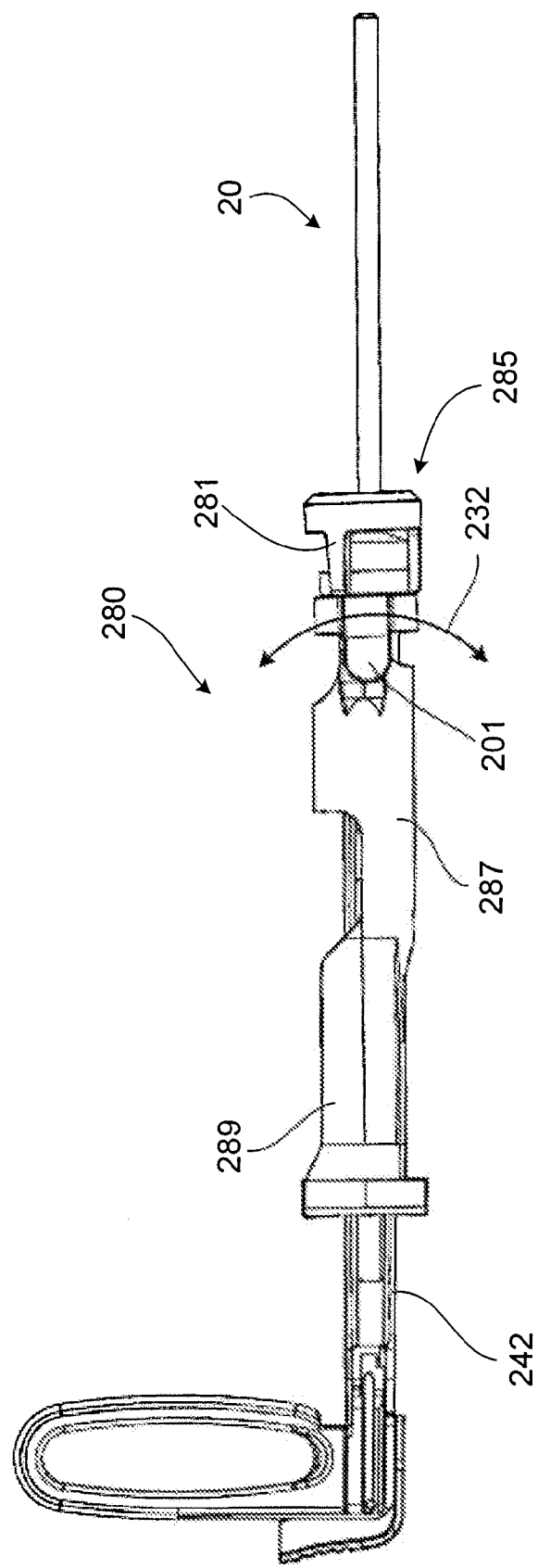
Figure 14D:
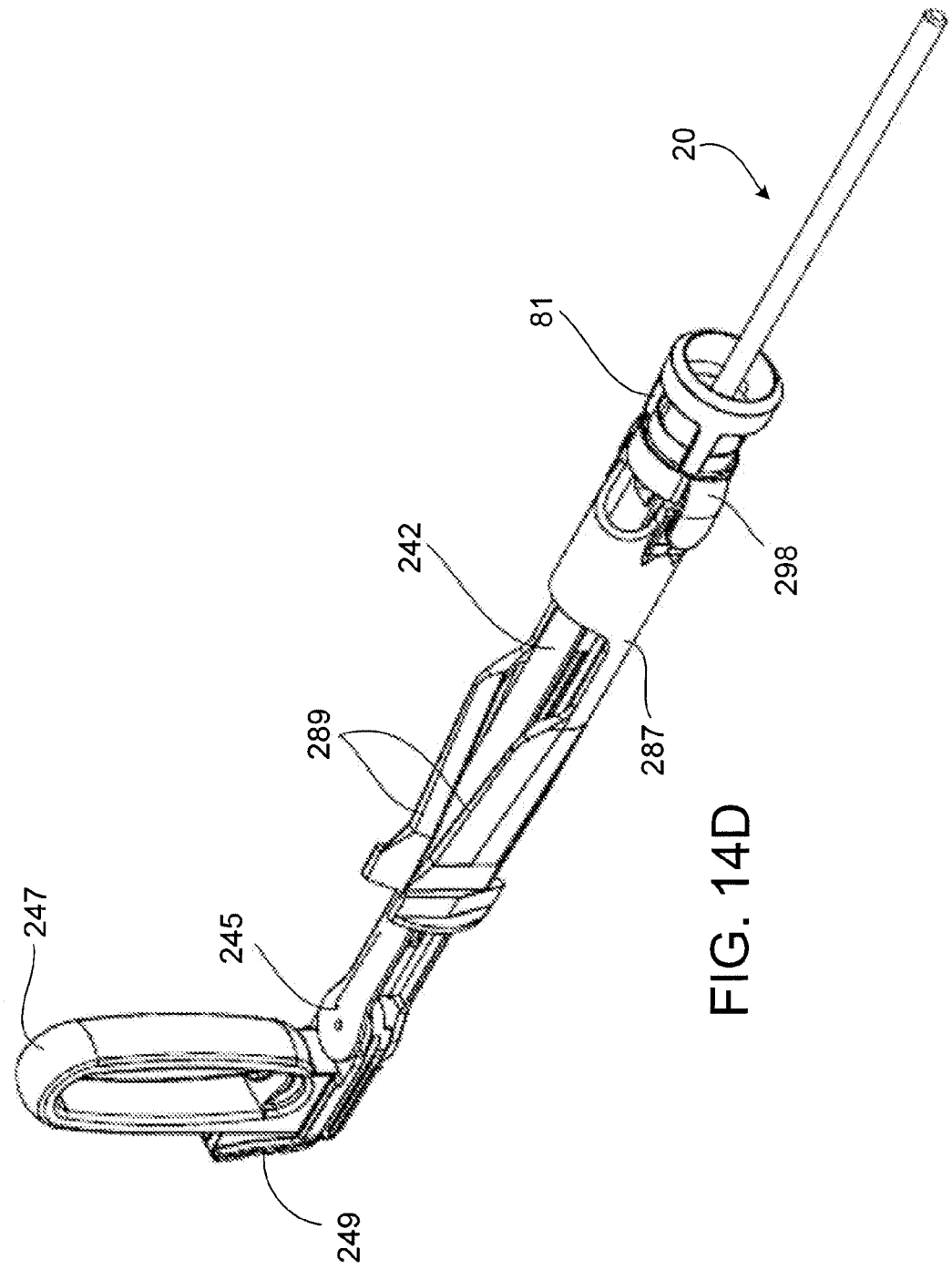

Referring to FIGS. 14A-14D, the colpotomizer cup 280 is loaded onto the manipulator handle 240 by advancing the colpotomizer cup 280 over manipulation tip at the distal end portion 244 of the frame 242, with the manipulator tip 20 passing through the proximal and distal ends 283, 285 of the annular body 281 (as illustrated in FIG. 14A) as the colpotomizer cup 280 is slid back towards the proximal end portion 243 of the frame 242. The locking member 249 is advanced along the frame 242 to a loaded position at a point beyond the recess 241, as illustrated in FIG. 14B. As shown in FIG. 14B, the sleeve 287 generally conforms to the shape of the frame 242. The colpotomizer cup 280 can then be pushed along the frame 242 towards the distal end portion 244 to a locked position in which the protrusions 290 (FIG. 12C) on the spring arms 289 engage the recess 241 in the frame 242. As shown in FIGS. 14C & 14D, in the locked position, the cup base 282 of the colpotomizer cup 280 circumferentially surrounds the tip base 21, of the manipulator tip 20, and the finger 22 extends outwardly through the distal end 285 of the colpotomizer cup 280. The pivotable connection between the cup base 282 and the sleeve 287 allows the colpotomizer cup 280 to move with the manipulator tip 20, which pivots, about point 201, relative to the frame 242, as illustrated by arrows 232 (FIG. 14C).

In some implementations, a vaginal occluder, such as the vaginal occulder described above with reference to FIG. 3, can be supported on the hinge adaptor 298.

Figure 15B:
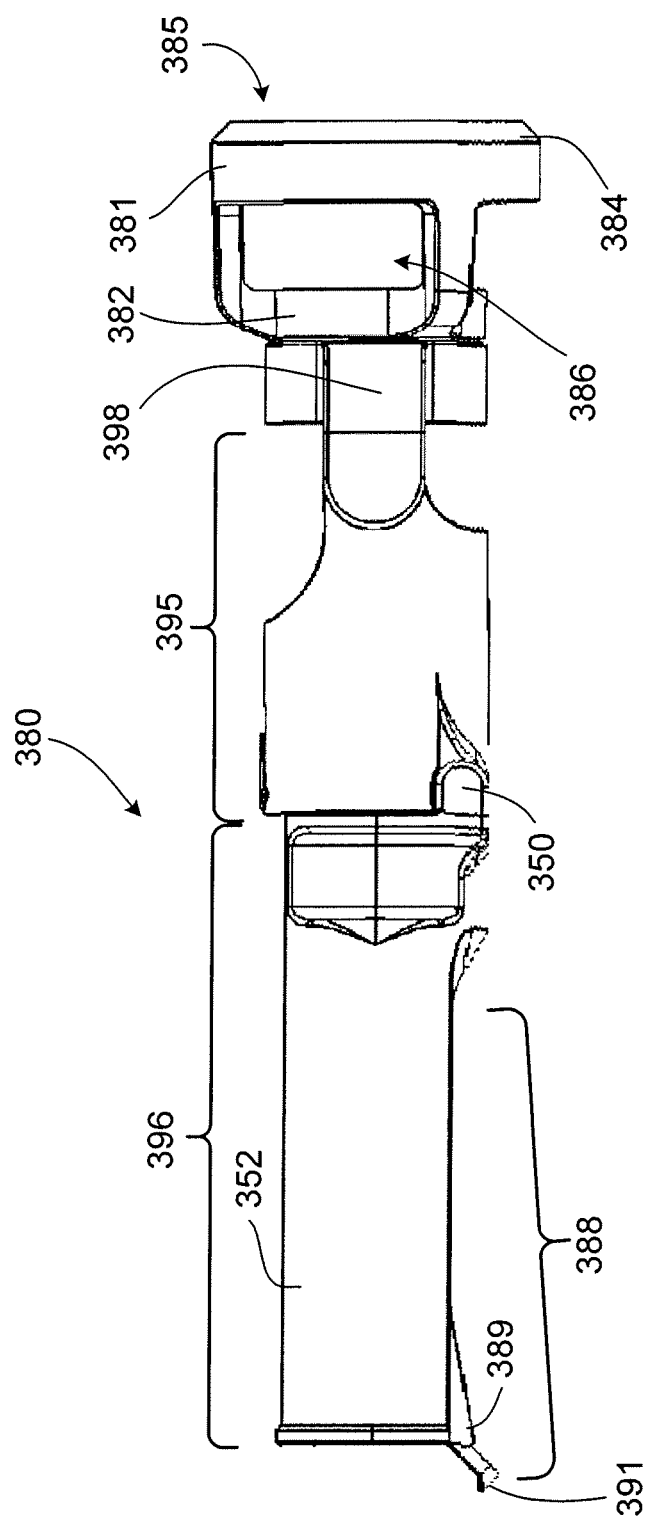
FIG. 15B is a side view of the colpotomizer cup of the colpotomizer cup of FIG. 15A.
Figure 15C:
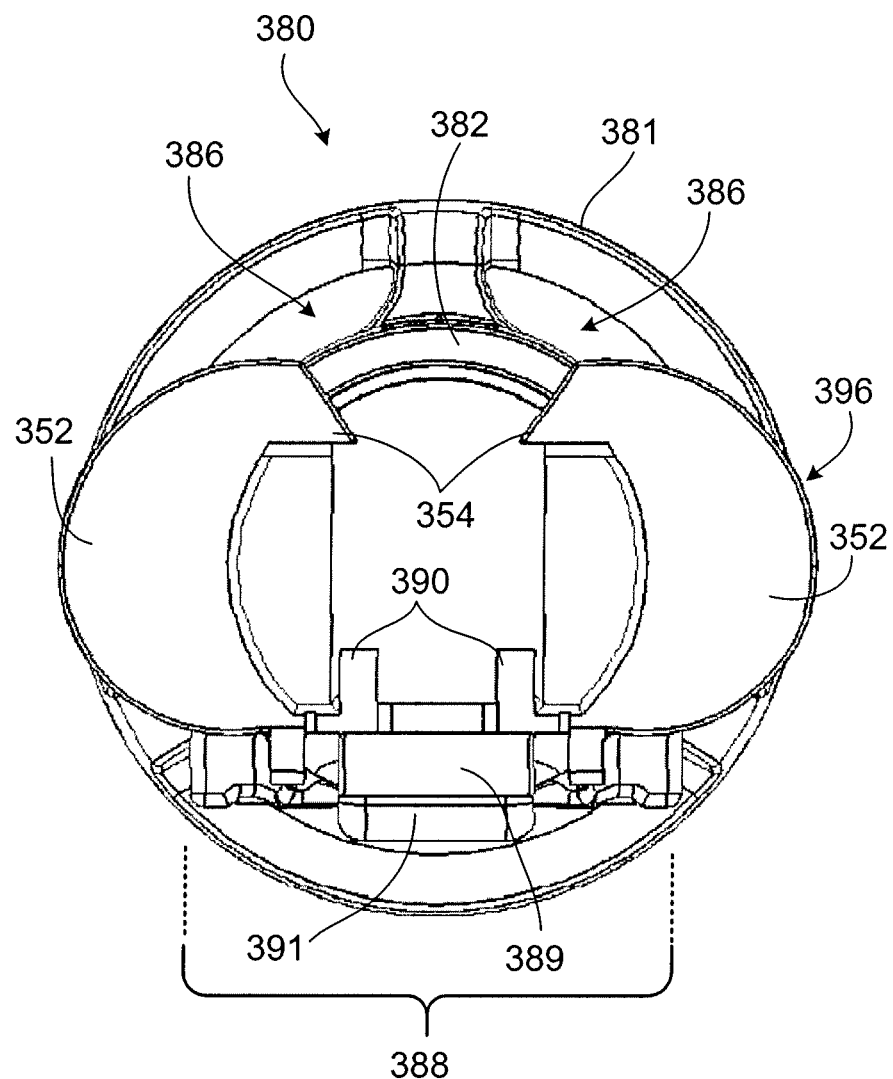
FIG. 15C is an end view of the colpotomizer cup of FIG. 12A.

FIGS. 15A-15D illustrate another implementation of a colpotomizer cup 380 configure for use with a uterine manipulator handle having a pivotable tip. FIGS. 15A through 15C illustrate an implementation of a colpotomizer cup 380 that includes an annular body 381 ("cup body"), a cup base 382 at a proximal end 383 and a rim 384 at a distal end 385. The rim 384 is beveled to permit anatomical landmark and incision backstop during use. Viewing windows 386 are provided in the annular body 381.

Figure 15D:
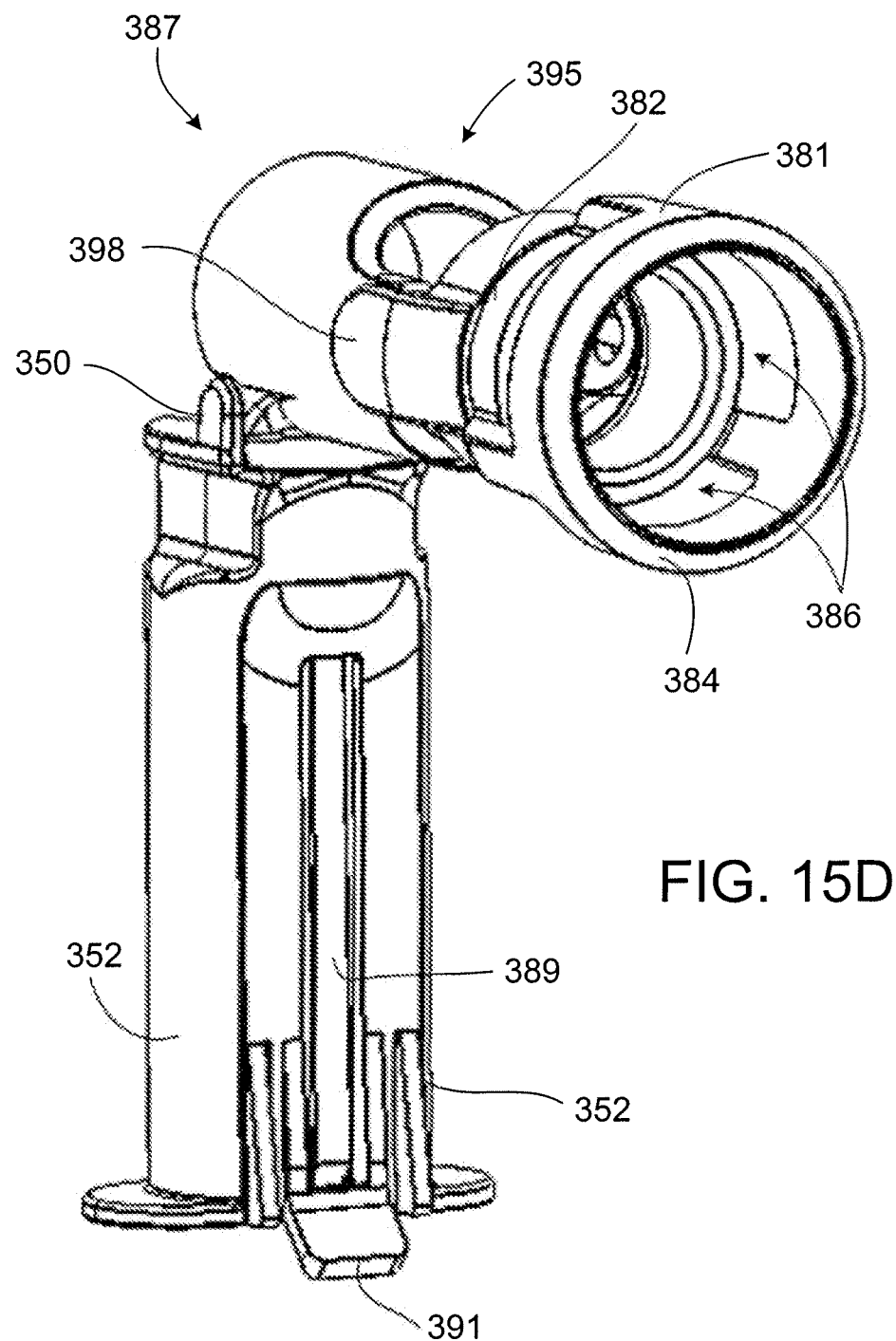
FIG. 15D is a perspective view of the colpotomizer cup of FIG. 15A showing a proximal end portion of the sleeve rotated at an angle of approximately 90° relative to a distal end portion of the sleeve.

A sleeve 387 is pivotably connected to the cup base 382 via a hinge adaptor 398. The hinge adaptor 398 allows the annular body 381 to be rotated relative to the sleeve 387, which allows the annular body 381 to move with a pivotable tip 20/tip hub 348 (FIGS. 16A & 16B) of a uterine manipulator handle 340. Notably, the sleeve 387 includes a distal end portion 395 and a proximal end portion 396 that are pivotably connected at a hinge 350, which may allow for easier assembly of the colpotomizer cup 380 with the uterine manipulator handle 340. As shown in FIG. 15D, the hinge 350 allows the proximal end portion 396 to pivot to a position at about 90° relative to the distal end portion 395.

The proximal end portion 396 includes a locking member 388. The locking member 388 consists of a cantilever arm 389, and a pair of sidewalls 352. The cantilever arm 389 includes a pair of protrusions 390 that are configured (e.g., sized and shaped) to engage a mating recess 341 (FIG. 16A) in the manipulator handle 340, for locking the colpotomizer cup 380 at a predetermined position along the length of the manipulator handle 340. The cantilever arm 389 also includes a finger tab 391 that can be engaged to release (disengage) the locking member 388. The sidewalls 352 are shaped to conform to a body 342 (FIG. 16A) of the manipulator handle 340. The sidewalls 352 include ridges 354, which overlay the body 342 of the manipulator handle 340 when the colpotomizer cup 380 is assembled with the manipulator handle 340.

The colpotomizer cup 380 is formed of material suitable for medical devices, that is, medical grade material. Plastics, such as polyvinylchloride, polycarbonate, polyolefins, polyproylene, polyethylene, or other suitable medical grade plastics, or metals, such as stainless steel or aluminum, can be used.

Figure 16A:
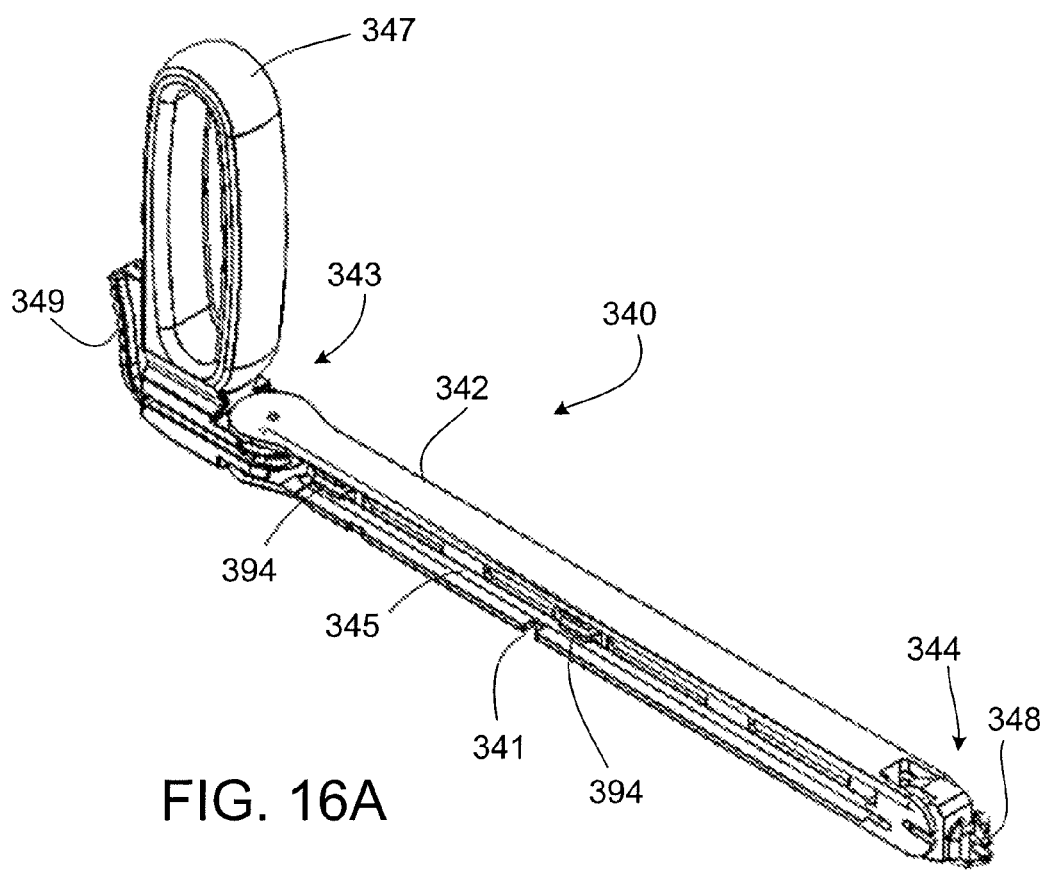
FIG. 16A is a perspective view of a manipulator handle having an articulable tip hub.
Figure 16B:
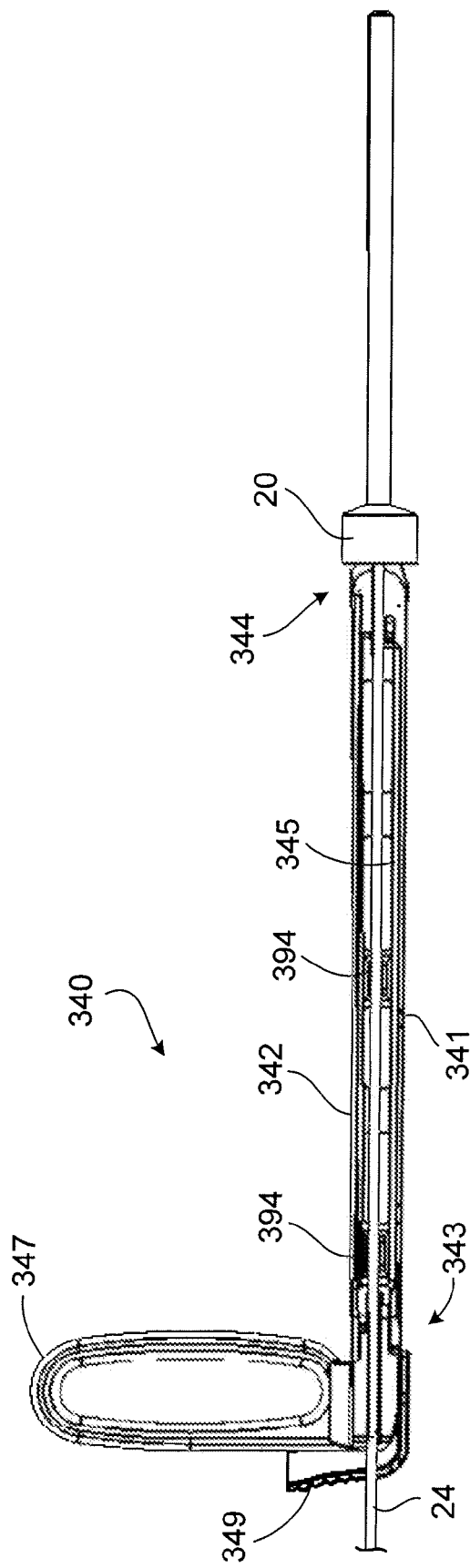
FIG. 16B is a side view of the manipulator handle of FIG. 16A with a manipulator tip mounted thereon.

FIGS. 16A-16B illustrate a manipulator handle 340 that can be used with the colpotomizer cup of FIGS. 15A-15D. As shown in FIG. 16A, the manipulator handle 340 includes an elongate frame 342, a grip 347, a tip hub 348, and a locking mechanism 349. The grip 347 is affixed in pivotal relationship to a proximal end portion 343 of the frame 342 and the tip hub 348 is affixed in pivotal relationship to a distal end portion 344 of the frame 342. A connecting structure 345 operatively couples the tip hub 348 to the grip 347 such that movement of the grip 347 relative to the frame 342 causes a corresponding movement of the tip hub 348 relative to the frame 342. The connecting structure can, for example, be a wire. The locking mechanism 349 is operable to fix the grip 347 against movement relative to the frame 342. A recess 341 is disposed along a length of the frame 340. The frame 342 also includes depressions 394, which can accommodate catheter tubing between the sleeve 387 and the uterine manipulator handle 340.

Referring to FIG. 16B, the tip hub 348 is configured to releasably receive and support a manipulator tip 20.

Figure 17A:
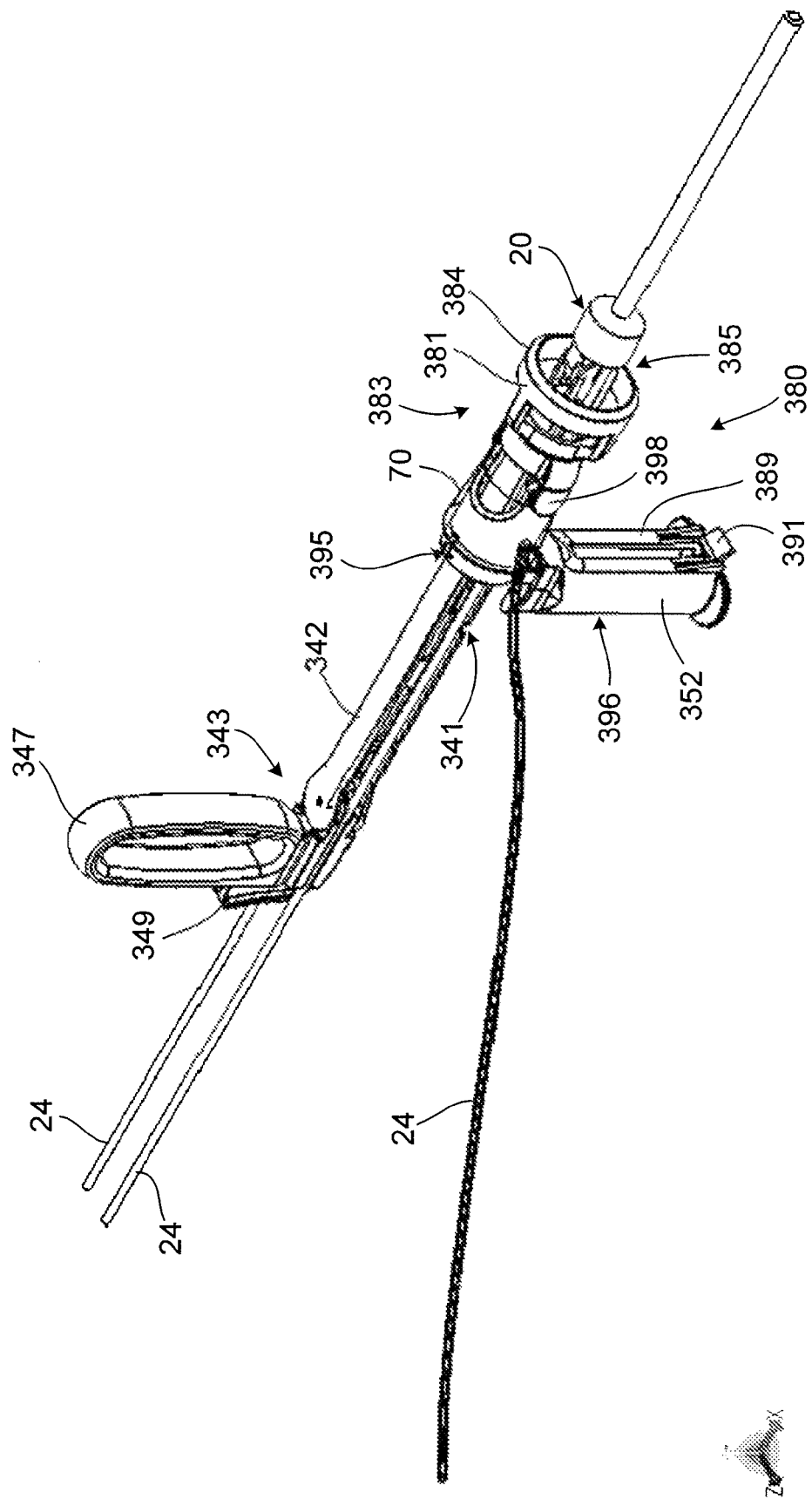
FIGS. 17A-17D illustrate assembly of the colpotomizer cup of FIG. 15A onto the manipulator handle of FIG. 16A.
Figure 17B:
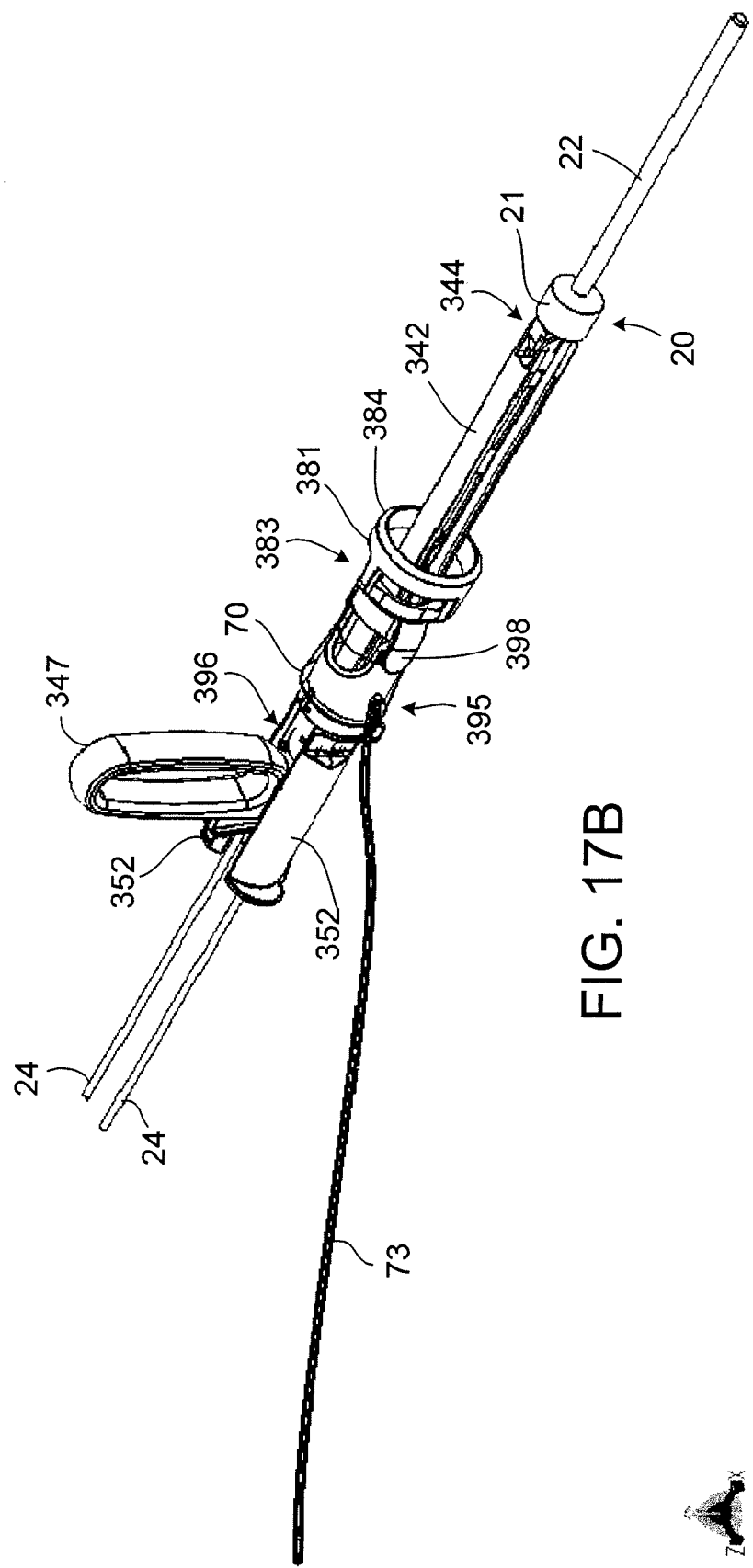

Referring to FIGS. 17A-17D, the colpotomizer cup 380 is loaded onto the manipulator handle 340 with the proximal end portion 396 arranged at angle of about 90° relative to the distal end portion 395. The distal end portion 395 of the colpotomizer cup 380 is advanced over the manipulator tip 20 at the distal end portion 344 of the frame 342, with the manipulator tip 20 passing through the proximal and distal ends 383, 385 of the annular body 381 as the distal end portion 395 of the colpotomizer cup 380 is slid back towards the proximal end portion 343 of the frame 342, as shown in FIG. 17A. Once the annular body 381 is advanced to a position beyond the manipulator tip 20, the proximal end portion 396 can be rotated towards a position in which the sidewalls 352 snap-up around the frame 342, and the sleeve 387 can be slid back further towards the proximal end portion 343 of the frame 342 into a loaded position, as shown in FIG. 17B.

Figure 17C:
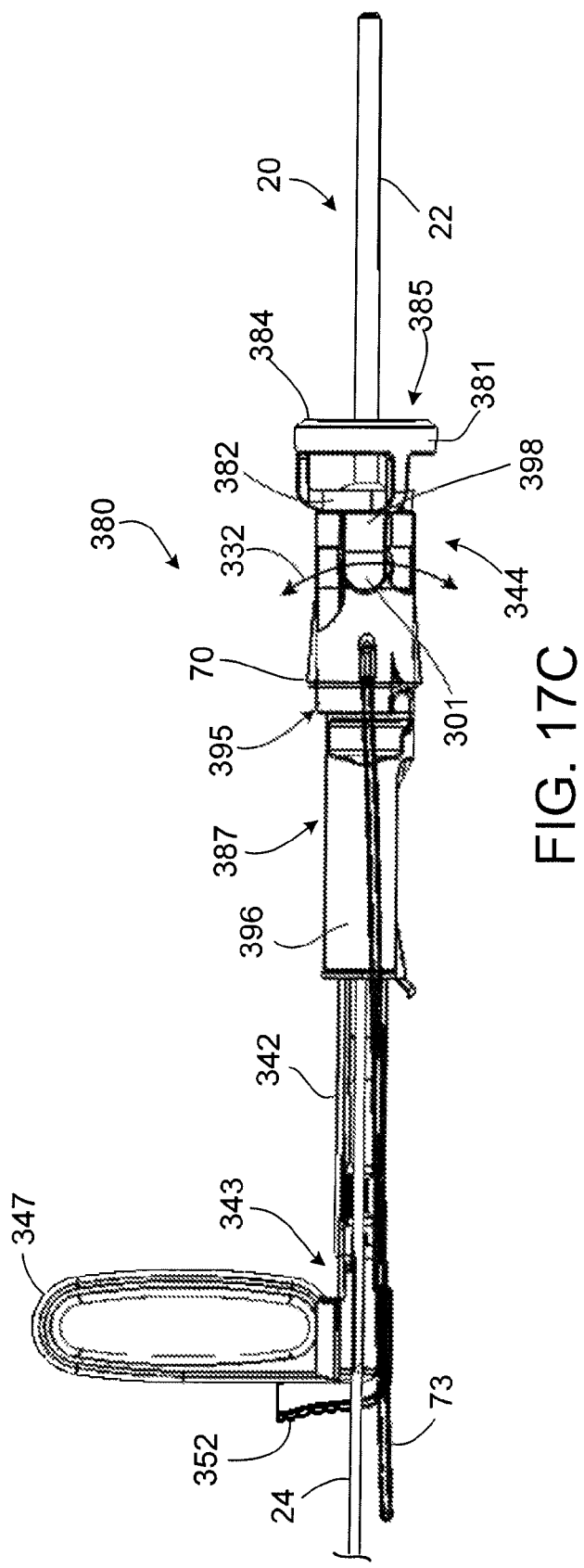
Figure 17D:
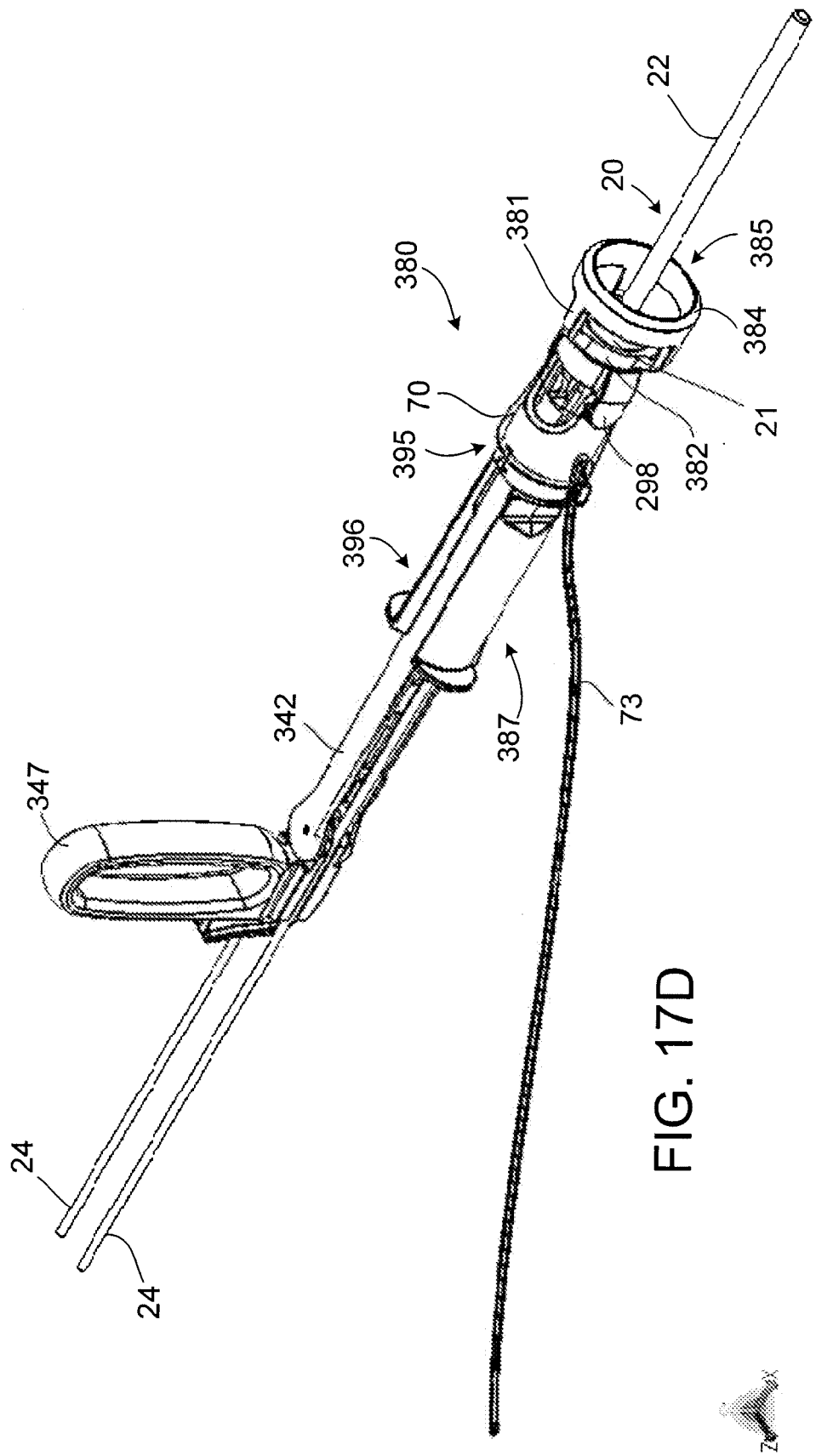

The colpotomizer cup 380 can then be pushed along the frame 342 towards the distal end portion 344 of the frame 342 to a locked position in which the protrusions 390 (FIG. 15C) on the cantilever arm 389 engage the recess 341 in the frame 342. As shown in FIGS. 17C & 17D, in the locked position, the cup base 382 of the colpotomizer cup 380 circumferentially surrounds the tip base 21 (FIG. 17B), of the manipulator tip 20, and the finger 22 extends outwardly through the distal end 385 of the colpotomizer cup 380. The pivotable connection between the cup base 382 and the sleeve 387 allows the colpotomizer cup 380 to move with the manipulator tip 20, which pivots, about point 301, relative to the frame 342, as illustrated by arrows 332 (FIG. 17C).

In some implementations, a vaginal occluder 70 can be supported on the colpotomizer cup 380 (e.g., on the hinge adaptor 398).

While implementations have been described in which the manipulator tip includes an expandable balloon on the finger, in some implementations, the finger does not include an expandable balloon.

Other implementations are within the scope of the following claims.

What is claimed is:

1. A colpotomizer cup comprising:
a cup body configured to receive a cervix; and
an elongate sleeve connected to the cup body via a first hinge that allows the cup body to pivot relative to the elongate sleeve,
wherein a proximal portion of the elongate sleeve is connected to a distal portion of the elongate sleeve via a second hinge that allows the proximal portion of the elongate sleeve to pivot relative to the distal portion of the elongate sleeve, and the proximal portion of the elongate sleeve comprises a locking member for locking the colpotomizer cup in a predetermined position along a length of a uterine manipulator handle.

2. The colpotomizer cup of claim 1, further comprising a vaginal occluder.

3. The colpotomizer cup of claim 1, wherein the locking member comprises a pair of spring arms.

4. The colpotomizer cup of claim 3, wherein the spring arms include protrusions.

5. The colpotomizer cup of claim 3, wherein the locking member includes finger tabs for displacing the spring arms to a disengaged position.

6. The colpotomizer cup of claim 1, wherein the locking member comprises a cantilever arm.

7. The colpotomizer cup of claim 2, wherein the vaginal occluder is disposed around a portion of the elongate sleeve.

8. A uterine manipulator comprising:
a uterine manipulator handle comprising an elongate shaft having a locking feature; and
a colpotomizer cup comprising:
a cup body configured to receive a cervix; and
an elongate sleeve connected to the cup body via a first hinge that allows the cup body to pivot relative to the elongate sleeve,
wherein a proximal portion of the elongate sleeve is connected to a distal portion of the elongate sleeve via a second hinge that allows the proximal portion of the elongate sleeve to pivot relative to the distal portion of the elongate sleeve, and the proximal portion of the elongate sleeve comprises a locking member configured to engage the locking feature of the elongate shaft of the uterine manipulator handle for locking the colpotomizer cup in a predetermined, locked position along a length of the uterine manipulator handle.

9. The uterine manipulator of claim 8, wherein the locking feature comprises a recess.

10. The uterine manipulator of claim 8, wherein the locking member comprises a pair of spring arms.

11. The uterine manipulator of claim 10, wherein the locking feature comprises a recess, and wherein the spring arms include protrusions adapted to engage the recess.

12. The uterine manipulator of claim 10, wherein the locking member includes finger tabs operable to disengage the protrusions from the recess.

13. The uterine manipulator of claim 8, wherein the locking member comprises a cantilever arm.

14. The uterine manipulator of claim 8, wherein a distal end portion of the elongate shaft is in the form of a frame that is configured to be inserted into a vagina, and a tip hub that is configured to releasably receive and support a manipulator tip is pivotally connected to a distal end portion of the frame.

15. The uterine manipulator of claim 14, wherein the manipulator handle further comprises a grip pivotally connected to a proximal end portion of the frame, wherein the grip is moveable relative to the frame to control movements of the tip hub relative to the frame.

16. The uterine manipulator of claim 15, wherein the grip is movable relative to the frame to control movements of the cup body relative to the frame when the colpotomizer cup is positioned in the locked position on the manipulator handle.

17. The uterine manipulator of claim 8, wherein the uterine manipulator comprises a manipulator tip, and wherein a cup base of the colpotomizer cup is arranged coaxially with a tip base of the manipulator tip when the colpotomizer cup is positioned in the locked position on the manipulator handle.

18. The uterine manipulator of claim 8, wherein the manipulator handle comprises an arcuate shaft.

19. The uterine manipulator of claim 8, wherein the colpotomizer cup comprises a vaginal occluder.

20. The uterine manipulator of claim 8, further comprising a manipulator tip mounted to the manipulator handle, wherein the locking member of the colpotomizer cup is configured to engage the locking feature of the uterine manipulator handle for locking the colpotomizer cup in a predetermined position relative to the manipulator tip.

21. The uterine manipulator of claim 8, further comprising a manipulator tip configured to be releasably coupled to the uterine manipulator handle.

22. The uterine manipulator of claim 21, wherein the manipulator tip has a tip base and a finger that extends from a surface of the tip base, and the tip base has a larger diameter than the finger such that the tip base is configured to abut a cervix of a patient when the manipulator tip is coupled to the uterine manipulator handle and the finger is inserted into a uterine cavity of the patient.

23. The uterine manipulator of claim 22, wherein the finger of the manipulator tip carries an expandable balloon to which a catheter is fluidly connected, the catheter being configured to be retained within a channel that extends along the elongate shaft of the uterine manipulator handle when the manipulator tip is releasably coupled to the uterine manipulator handle.

24. The uterine manipulator of claim 22, wherein the colpotomizer cup matingly engages the tip base of the uterine manipulator tip when the colpotomizer cup is in the predetermined, locked position.

25. The uterine manipulator of claim 8, wherein the uterine manipulator handle further comprises a tip hub extending from a distal end portion of the elongate shaft, and a tip base of the manipulator tip is configured to matingly engage the tip hub of the uterine manipulator handle to releasably couple the manipulator tip to the uterine manipulator handle.

26. The uterine manipulator of claim 19, wherein the vaginal occluder is disposed around a portion of the elongate sleeve.

27. A uterine manipulator comprising:
a uterine manipulator handle comprising an elongate shaft having a locking feature;
a manipulator tip configured to be releasably coupled to the uterine manipulator handle, the manipulator tip having a tip base and a finger that extends from a surface of the tip base, and the tip base having a larger diameter than the finger such that the tip base is configured to abut a cervix of a patient when the manipulator tip is coupled to the uterine manipulator handle and the finger is inserted into a uterine cavity of the patient; and
a colpotomizer cup comprising:
a cup body configured to receive a cervix; and
an elongate sleeve connected to the cup body via a first hinge that allows the cup body to pivot relative to the elongate sleeve,
wherein a proximal portion of the elongate sleeve is connected to a distal portion of the elongate sleeve via a second hinge that allows the proximal portion of the elongate sleeve to pivot relative to the distal portion of the elongate sleeve, and the proximal portion of the elongate sleeve comprises a locking member configured to engage the locking feature of the elongate shaft of the uterine manipulator handle for locking the colpotomizer cup in a predetermined, locked position along a length of the uterine manipulator handle.

* * * * *